(12) United States Patent
Fujii et al.

(10) Patent No.: US 6,186,970 B1
(45) Date of Patent: Feb. 13, 2001

(54) PROTECTIVE CLOTHING FOR REGIONS OF LOWER LIMB

(75) Inventors: Takako Fujii; Risa Saka, both of Kyoto (JP)

(73) Assignee: Wacoal Corp. (JP)

(*) Notice: Under 35 U.S.C. 154(b), the term of this patent shall be extended for 0 days.

(21) Appl. No.: 09/194,646

(22) PCT Filed: Sep. 22, 1997

(86) PCT No.: PCT/JP97/03372

§ 371 Date: Dec. 1, 1998

§ 102(e) Date: Dec. 1, 1998

(87) PCT Pub. No.: WO98/43504

PCT Pub. Date: Oct. 8, 1998

(30) Foreign Application Priority Data

Apr. 1, 1997 (JP) .................................................. 9-83120

(51) Int. Cl.$^7$ .................................................. A61L 15/00
(52) U.S. Cl. .................................. 602/75; 602/63; 2/22
(58) Field of Search ................................ 602/75, 65, 63; 2/22

(56) References Cited

U.S. PATENT DOCUMENTS 5,109,546 * 5/1992 Dicker .
5,367,708 * 11/1994 Fujimoto .
5,640,714 * 6/1997 Tamaka .

FOREIGN PATENT DOCUMENTS

| 4050302 | 2/1992 | (JP) . |
| 4057902 | 2/1992 | (JP) . |
| 4057904 | 2/1992 | (JP) . |
| 4343868 | 11/1992 | (JP) . |
| 8081807 | 3/1996 | (JP) . |
| 9241906 | 9/1997 | (JP) . |

* cited by examiner

*Primary Examiner*—Michael A. Brown
*Assistant Examiner*—Lalita Hamilton
(74) *Attorney, Agent, or Firm*—Morrison Law Firm

(57) ABSTRACT

The present invention provides a leg protection garment that is effective for mainly supporting the hamstrings, the muscle of the posterior side of the femoral region among the leg portion. The leg protection garment having a lower half of the body part which has a leg portion of length capable of covering at least the patella region and formed of stretchable fabric, the garment having a portion having a partially strong straining force, the portion having a strong straining force comprising at least a portion having a strong straining force 101 (A) which ranges from an area above the trochanter major to the vicinity 5 of the upper end of the tibia by way of the trochanter major and further the vicinity over the boundary between the musculus biceps femoris and the tractus iliotibialis so as to support the musculus biceps femoris, wherein the portion obliquely crosses the vicinity 4 of the tendon region located below the muscle belly of the musculus biceps femoris without crossing the muscle belly of the musculus biceps femoris.

45 Claims, 40 Drawing Sheets

PROTECTIVE CLOTHING FOR REGIONS OF LOWER LIMB

TECHNICAL FIELD

The present invention relates to a leg protection garment.

More particularly, it relates to a leg protection garment applied generally in close contact with the surface of the human body and is mainly effective for supporting the hamstrings, namely, the muscles of the posterior side of the femoral region of the leg.

BACKGROUND ART

Hitherto, various kinds of sports or training activities or the like excessively load muscles of the leg region and often cause disorders in this region. In order to prevent such disorders in muscles, or to support the relevant muscles or bones when disorders occur, a taping treatment or so-called supporter has been employed. However, the above mentioned conventional taping method has a problem, for example, applying the taping treatment requires skill etc. Moreover, the taping treatment inhibits the movement of the muscles to prevent excessive contraction. On the other hand, the supporter, worn over the articulation, also restricts the movement of the articulation, and in turn often indirectly inhibits the movement of muscles. Therefore, both the taping treatment and the supporter restrict the function of muscles and do not provide support for the contraction of muscles.

Thus, a leg protection garment having a structure for supporting the specific muscles of the leg by a portion having a strong straining force has been developed (See Publication of Japanese Patent Application (Tokkai Hei) No. 4-343868, (Tokko Hei) No.6-41641, (Tokko Hei) No. 6-51921). These leg protection garments: can be put on easily and adequately by ordinary people; provide a comfortable fit without being painful to a user; have no hygienic problems such as itchy skin due to it becoming stuff; and furthermore support the muscle contraction and help the extended muscle easily recover, thus being effective for reducing muscle fatigue during exercise and exhibiting the effect of promoting the prevention or treatment of specific disorders etc. of the leg.

Moreover, the leg protection garment described in the above mentioned official gazettes support the muscles of the medial, lateral and anterior sides of the femoral region, or the muscle below the patella region. Among such muscles, the musculus quadriceps femoris, for example, functions by flexing the articulatio coxae and extending the articulatio genus. However, the articulatio genus becomes unstable when it is in the extended position, so that an impact can easily cause a rupture of the ligament and a fracture in the vicinity of the articulation. Therefore, by supporting the musculus quadriceps femoris, its function can be strengthened and the above mentioned disorders can be prevented.

However, as mentioned above, the conventional leg protection garment supports only the medial, lateral and anterior sides of the femoral region, but does not support the hamstrings, i.e. the muscles of the posterior side of the femoral region. Herein, the hamstrings means the muscles of the posterior side of the femoral region, namely, the combination of the musculus biceps femoris, the musculus semitendinosus, and the musculus semimembranosus. These muscles are mainly used, for example,: ① when strongly stepping backward on the ground in running, particularly, in increasing the running speed; ② when jumping higher in jumping; and ③ when raising up on a bicycle pedal after pushing it downward. These muscles have functions of extending the articulatio coxae and flexing or adducting the articulatio genus. The hamstrings, because of their function, also play important roles in various sports, for example, rugby, soccer, basketball, volley ball, baseball, golf, bicycle racing, bobsledding, etc. For example, in the movement of running quickly after the scrum and break in rugby, if the posterior side of the femur is not used well, it is necessary to switch the stressed place from the anterior side to the posterior side, and so a smooth movement cannot be conducted. Also, the same is true in the play following a rebound while playing basketball. In other words, the musculus extensor of articulatio coxae plays an important role in providing stability of the pelvis in the front and back directions, and is particularly involved in the extension of the extensor muscle of articulatio coxae during normal walking. In sports in which players strike the ground with their feet (running, basketball, volley ball, etc.), if the pelvis position moves upward and downward, power disperses and the subsequent motion cannot be smoothly conducted. Moreover, in some aspects of jumping while playing volley ball, if players can jump without bending the knee deeply, it is advantageous that they can jump by taking the speed of support running. In such a case, it is necessary to jump by mainly using the posterior side of the femur. Furthermore, in bobsledding, the first pushing start is a key to the subsequently attained speed. The muscles used during this first pushing start are hamstrings. Thus, hamstrings have important functions in various kinds of sports. However, it is generally indicated that, in Japanese people, the hamstrings are weaker than the muscles of the anterior side of the femoral region such as the musculus quadriceps femoris, etc.

DISCLOSURE OF THE INVENTION

It is the object of the present invention to provide a garment which has a structure in which a tape-like portion having a stronger straining force than stretchable fabric is partially placed on a garment's main part having at least lower half of the body and being formed of stretchable fabric and thus mainly provide support the muscle movement of the hamstrings, i.e. the muscles of the posterior side of the femoral region among the leg, which are not supported by the conventional leg protection garment.

Moreover, the leg position in which the articulatio genus is flexing is unstable and easily causes disorders in the ligament of the knee or the meniscus. Such disorders tend to occur in sports activities, for example, rugby or soccer, requiring a force generated by flexing the knee. Therefore, it is also an object of the present invention to prevent such disorders by supporting the hamstrings as mentioned above.

Furthermore, the function of the articulatio genus can be well balanced when each muscle of the anterior side and posterior side of the femoral region works sufficiently well. Balance such as this cannot sufficiently be attained with the conventional leg protection garments described in Japanese Patent Application No. Tokkai Hei 4-343868, No. Tokko Hei 6-41641, and No. Tokko Hei 6-51921, since they only aim at supporting the muscles of the anterior side of the femoral region. Therefore, it is also an object of the present invention is to aid the function of the articulatio genus and entire region of the articulatio coxae, by supporting not only the muscle of the anterior side of the femoral region but also the muscle of the posterior side of the femoral region by combining the garment of the present invention with the conventional leg protection garment.

In order to resolve the above mentioned problems, the present invention provides:

(1) a leg protection garment having a lower half of the body part that has a leg portion of length capable of covering at least the patella region and formed of stretchable fabric, wherein the garment has a portion having a partially strong straining force and comprises the portion expressed by at least the following (A) and/or (B) as the portion having a strong straining force;

(A) a portion having a strong straining force which ranges from an area above the trochanter major 1 to the vicinity 5 of the upper end of the tibia by way of the trochanter major 2 and further the vicinity over the musculus biceps femoris and/or the tractus iliotibialis so as to support the musculus biceps femoris, wherein the portion passes the vicinity 4 of the tendon region located below the muscle belly of the musculus biceps femoris without crossing the muscle belly of the musculus biceps femoris at a right angle with respect to the direction of the muscle fiber;

(B) a portion having a strong straining force that ranges from an area 11 above the musculus semimembranosus to the vicinity 14 of the upper end of the fibula by way of the vicinity over the musculus semimembranosus and/or the musculus adductor magnus so as to support the musculus semitendinosus and the musculus semimembranosus, wherein the portion passes the vicinity 13 of the tendon region located below the muscle belly of both the musculus semitendinosus and the musculus semimembranosus without crossing the muscle belly of the musculus semitendinosus and the musculus semimembranosus at a right angle with respect to the direction of the muscle fiber.

Moreover, it is preferable in the above mentioned leg protection garment that the portion (A) is a portion having a strong straining force that ranges from an area above the trochanter major 1 to the vicinity 6 of the upper end of the tibia by way of the trochanter major 2 and further the vicinity 3 over the boundary between the musculus biceps femoris and the tractus iliotibialis so as to support the musculus biceps femoris, wherein the portion obliquely crosses the vicinity 4 of the tendon region located below the muscle belly of the musculus biceps femoris without crossing the muscle belly of the musculus biceps femoris. And it is preferable that the portion (B) is a portion having a strong straining force which ranges from an area 11 above the musculus semimembranosus to the vicinity 14 of the upper end of the fibula by way of the vicinity 12 over the boundary between the musculus semimembranosus and the musculus adductor magnus so as to support the musculus semitendinosus and the musculus semimembranosus, wherein the portion obliquely crosses the vicinity 13 of the tendon region located below the muscle belly of both the musculus semitendinosus and the musculus semimembranosus without crossing the muscle belly of the musculus semitendinosus and the musculus semimembranosus.

Moreover, in the above mentioned leg protection garment, the following embodiments (I), (II) and (III) are mentioned as preferable embodiments: (I) an embodiment in which the portion (A) further has a portion having a strong straining force that, in an area above the trochanter major, passes over at least one muscle selected from the group consisting of the musculus tensor fasciae latae, the tractus iliotibialis, and the musculus glutaeus medius (preferably in the portion 6 over the musculus tensor fasciae latae); (II) an embodiment in which the portion (A) further has a portion having a strong straining force which ranges from the vicinity 5 of the upper end of the tibia to the vicinity 7 of the attaching region of the musculus semitendinosus and the musculus semimembranosus; and (III) an embodiment in which the portion (B) further has a portion having a strong straining force that ranges from the vicinity 14 of the upper end of the fibula to the vicinity 16 of an area above the ankle by way of the vicinity over the musculus gastrocnemius and/or the musculus soleus (preferably in the vicinity 15 over the boundary between the musculus gastrocnemius and the musculus soleus) so as to support the musculus gastrocnemius and the musculus soleus.

Furthermore, the leg protection garment of the present invention is:

(2) a leg protection garment having a lower half of the body part which has a leg portion of length capable of covering at least the patella region and formed of stretchable fabric, wherein the garment has a portion having a partially strong straining force and comprises the portion expressed by at least the following (A) and (B') as the portion having a strong straining force;

(A) a portion having a strong straining force that ranges from an area above the trochanter major 1 to the vicinity 5 of the upper end of the tibia by way of the trochanter major 2 and further the vicinity over the musculus biceps femoris and/or the tractus iliotibialis so as to support the musculus biceps femoris from the side, wherein the portion passes the vicinity 4 of the tendon region located below the muscle belly of the musculus biceps femoris without crossing the muscle belly of the musculus biceps femoris at a right angle with respect to the direction of the muscle fiber;

(B') a portion having a strong straining force which ranges from the vicinity 13 of the tendon region located below the muscle belly of both the musculus semitendinosus and the musculus semimembranosus to the vicinity 14 of the upper end of the fibula.

Moreover, it is preferable in the above mentioned leg protection garment that the portion (A) has a portion having a strong straining force ranging from an area above the trochanter major 1 to the vicinity 5 of the upper end of the tibia by way of the trochanter major 2 and further the vicinity 3 over the boundary between the musculus biceps femoris and the tractus iliotibialis so as to support the musculus biceps femoris, wherein the portion obliquely crosses the vicinity 4 of the tendon region located below the muscle belly of the musculus biceps femoris without crossing the muscle belly of the musculus biceps femoris.

Moreover, in the above mentioned leg protection garment, the following embodiments (I), (II), and (III) can also be mentioned as preferable embodiments:

(I) an embodiment in which the portion (A) further has a portion having a strong straining force that, in an area above the trochanter majors, passes over at least one muscle selected from the group consisting of the musculus tensor fasciae latae, the tractus iliotibialis, and the musculus glutaeus medius (preferably the portion 6 over musculus tensor fasciae latae);

(II) an embodiment in which the portion (A) further has a portion having a strong straining force which ranges from the vicinity 5 of the upper end of the tibia to the vicinity 7 of the attaching region of the musculus semitendinosus and the musculus semimembranosus; and (III) an embodiment in that the portion (B') further has a portion having a strong straining force which ranges from the vicinity 14 of the upper end of the fibula to the vicinity 16 of an area above the ankle by way of the vicinity over the musculus gastrocnemius and/or the musculus soleus (preferably in the vicinity 15 over the boundary between the musculus gastrocnemius and the musculus soleus) so as to support the musculus gastrocnemius and the musculus soleus.

Furthermore, a leg protection garment of the present invention is:

(3) a leg protection garment having a lower half of the body part that has a leg portion of length capable of covering at least the patella region and formed of stretchable fabric, wherein the garment has a portion having a partially strong straining force and comprises the portion expressed by at least the following (A') and (B) as the portion having a strong straining force;

(A') a portion having a strong straining force that ranges from the vicinity 4 of the tendon region located below the muscle belly of the musculus biceps femoris to the vicinity 5 of the upper end of the tibia;

(B) a portion having a strong straining force which ranges from an area 11 above the musculus semimembranosus to the vicinity 14 over the upper end of the fibula by way of the vicinity over the musculus semimembranosus and/or the musculus adductor magnus so as to support the musculus semitendinosus and the musculus semimembranosus, wherein the portion passes in the vicinity 13 of the tendon region located below the muscle belly of both the musculus semitendinosus and the musculus semimembranosus without crossing the muscle belly of the musculus semitendinosus and the musculus semimembranosus at a right angle with respect to the direction of the muscle fiber.

Moreover, it is preferable in the above mentioned leg protection garment that the portion (B) is a portion having a strong straining force which ranges from an area 11 above the musculus semimembranosus to the vicinity 14 over the upper end of the fibula by way of the vicinity 12 over the boundary between the musculus semimembranosus and the musculus adductor magnus so as to support the musculus semitendinosus and the musculus semimembranosus, wherein the portion obliquely crosses the vicinity 13 of the tendon region located below the muscle belly of both the musculus semitendinosus and the musculus semimembranosus without crossing the muscle belly of the musculus semitendinosus and the musculus semimembranosus.

Moreover, in the above mentioned leg protection garment, the following embodiments (I) and (II) are mentioned as preferable embodiments:

(I) an embodiment in which the portion (A') further has a portion having a strong straining force ranging from the vicinity 5 of the upper end of the tibia to the vicinity 7 over the attaching region of the musculus semitendinosus and the musculus semimembranosus;

(II) an embodiment in which the portion (B) further has a portion having a strong straining force that ranges from the vicinity 14 of the upper end of the fibula to the vicinity 16 of an area above the ankle by way of the vicinity over the musculus gastrocnemius and/or the musculus soleus (preferably in the vicinity 15 over the boundary between the musculus gastrocnemius and the musculus soleus) so as to support the musculus gastrocnemius and the musculus soleus.

(4) It is also preferable that the leg protection garment of the present invention further have a portion having a strong straining force (C) comprising a portion having a strong straining force which ranges from the upper region of the lateral crus 21 located slightly below the patella region to the vicinity 16 of an area above the ankle by way of the vicinity of the musculus gastrocnemius and/or the musculus soleus (preferably in the vicinity 15 over the boundary between the musculus gastrocnemius and the musculus soleus) so as to support the musculus gastrocnemius and the musculus soleus; and a portion having a strong straining force that ranges from the upper region of the medial crus 22 located slightly below the patella region to the vicinity 24 of an area above the ankle by way of the vicinity over the musculus gastrocnemius and/or the musculus soleus (preferably in the vicinity 23 over the boundary between the musculus gastrocnemius and the musculus soleus) so as to support the musculus gastrocnemius and the musculus soleus.

(5) It is also preferable that the leg protection garment of the present invention further have a portion having a strong straining force (D) comprising a lateral portion which ranges from the vicinity of the trochanter major to the patella region 35 by way of the vicinity over the tractus iliotibialis and/or the musculus vastus lateralis, and further ranges from the patella region 35 to the vicinity 16 of an area above the ankle by way of the vicinity over the musculus gastrocnemius and/or the musculus soleus so as to support the musculus gastrocnemius and the musculus soleus; and a medial portion that ranges from the medial side of the femur 38 to the patella region 35 by way of the musculus vastus medialis 39 so as to support the musculus vastus medialis, and which further ranges from the patella region 35 to the vicinity 43 of an area above the ankle by way the vicinity over the musculus gastrocnemius and/or the musculus soleus so as to support the. musculus gastrocnemius and the musculus soleus.

Moreover, it is specifically preferable that the portion (D) comprises the lateral portion that ranges from the trochanter major 2 to the side face of the patella region 35 by way of the vicinity of the tractus iliotibialis 33 and the musculus vastus lateralis 34, and further ranges from the side face of the patella region 35 to the vicinity 16 of an area above the ankle by way of the vicinity over the boundary between the musculus gastrocnemius and the musculus soleus so as to support the musculus gastrocnemius and the musculus soleus; and the medial portion that ranges from the medial side of the femur 38 to the side face of the patella region 35 by way of the portion 39 over musculus vastus medialis without crossing the muscle belly of the musculus vastus medialis so as to support the musculus vastus medialis, and further ranges from the side face of the patella region 35 to the vicinity 43 of an area above the ankle by way of the vicinity 42 over the boundary between the musculus gastrocnemius and the musculus soleus so as to support the musculus gastrocnemius and the musculus soleus.

(6) It is also preferable that the leg protection garment of the present invention further have a portion having a strong straining force (D') comprising a lateral portion which ranges from the outside 31 of the hip to the patella region 35 by way of the portion 32 over the musculus glutaeus maximus, the trochanter major 2 and the vicinity over the tractus iliotibialis and/or the musculus vastus lateralis, and further ranges from the patella region 35 to the vicinity 16 of an area above the ankle by way of the vicinity over the musculus gastrocnemius and/or the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and further ranges from the patella region 35 to the vicinity 43 of an area above the ankle by way of the vicinity over the musculus gastrocnemius and/or the musculus soleus so as to support the musculus gastrocnemius and the musculus soleus.

Moreover, it is specifically preferable that the portion (D') comprises a lateral portion which ranges from the outside 31 of the hip to the side face of the patella region 35 by way of the portion 32 over the musculus glutaeus maximus, the trochanter major 2, the vicinity 33 over the tractus iliotibialis and the vicinity 34 over the musculus vastus lateralis, and further ranges from the side face of the patella region 35 to the vicinity 16 of an area above the ankle by way of the vicinity 15 of the boundary between the musculus gastrocnemius and the musculus soleus so as to support the musculus gastrocnemius and the musculus soleus; and the medial portion which ranges from the medial side 38 of the femur to the side face of the patella region 35 by way of the portion 39 over the musculus vastus medialis without crossing the muscle belly of the musculus vastus medialis so as to support the musculus vastus medialis, and further ranges from the side face of the patella region 35 to the vicinity 43 of an area above the ankle by way of the vicinity 42 over the boundary between the musculus gastrocnemius and the musculus soleus 80 as to support the musculus gastrocnemius and the musculus soleus.

(7) It is also preferable that the leg protection garment of the present invention further have the portion (E) ranging from the upper region 51 of the lateral crus located slightly below the patella region to the vicinity 54 of an area above the ankle by way of the vicinity over the musculus gastrocnemius and/or the musculus soleus so as to support the musculus gastrocnemius and the musculus soleus, wherein the portion passes the vicinity of the tendon region located below the musculus gastrocnemius without crossing the muscle belly of the musculus gastrocnemius at the right angle with respect to the direction of the muscle fiber.

Moreover, it is specifically preferable that the portion (E) ranging from the upper region 51 of the lateral crus located slightly below the patella region to the vicinity 54 of an area above the ankle by way of the vicinity 52 over the boundary between the musculus gastrocnemius and the musculus soleus 80 as to support the musculus gastrocnemius and the musculus soleus, wherein the portion obliquely crosses the tendon region 53 located below the muscle belly of the musculus gastrocnemius without crossing the muscle belly of the musculus gastrocnemius.

(8) Furthermore, it is preferable in the leg protection garment of the present invention that the portion having a strong straining force is formed in a way in which a predetermined shaped stretchable fabric is overlapped with the garment's main part by stitching or adhering.

(9) Furthermore, it is preferable in the leg protection garment of the present invention that the portion having a strong straining force is formed in a way in which a predetermined shaped stretchable fabric is stretched and overlapped with the garment's main part by stitching or adhering.

(10) Furthermore, it is preferable in the leg protection garment of the present invention that the portion having a strong straining force is formed in a way in which elastic resin is impregnated or elastic resin film is adhered to a predetermined location of the garment's main part.

(11) Furthermore, it is preferable in the leg protection garment of the present invention that the portion having a strong straining force is a portion using an elastic fiber having a thicker thickness than that of any other location in fiber material constituting the garment's main part.

(12) Furthermore, it is preferable in the leg protection garment of the present invention that the portion having a strong straining force is a portion which comprises texture of a knitted fabric having a stronger straining force than texture of a knitted fabric of stretchable fabric constituting the garment's main part.

(13) Furthermore, it is preferable in the leg protection garment of the present invention that the portion having a strong straining force has a straining force of 30 to 400 gf.

(14) Furthermore, it is preferable in the leg protection garment of the present invention that the stretchable fabric is a knitted fabric selected from the group consisting of a two direction stretchable tricot knitted fabric and a stretchable rochelle knitted fabric.

BREIF DESCRIPTION OF DRAWINGS

BEST MODE FOR CARRYING OUT THE INVENTION

Hereinafter, the specific embodiments of the present invention will be explained with reference to the figures. In the present invention, when we explain where in the garment of the present invention a portion having a strong straining force primarily exhibiting a taping function is located, that is, the location in the garment where the portion having a strong straining force is located, we often use the names of the body regions or the portions corresponding to the muscles or the skeleton. Therefore, for ease of understanding, first we will explain the locations on the skeleton and the muscles of the human body, which we use for explaining the location numbers of the portions having a strong straining force.

Figure 39:
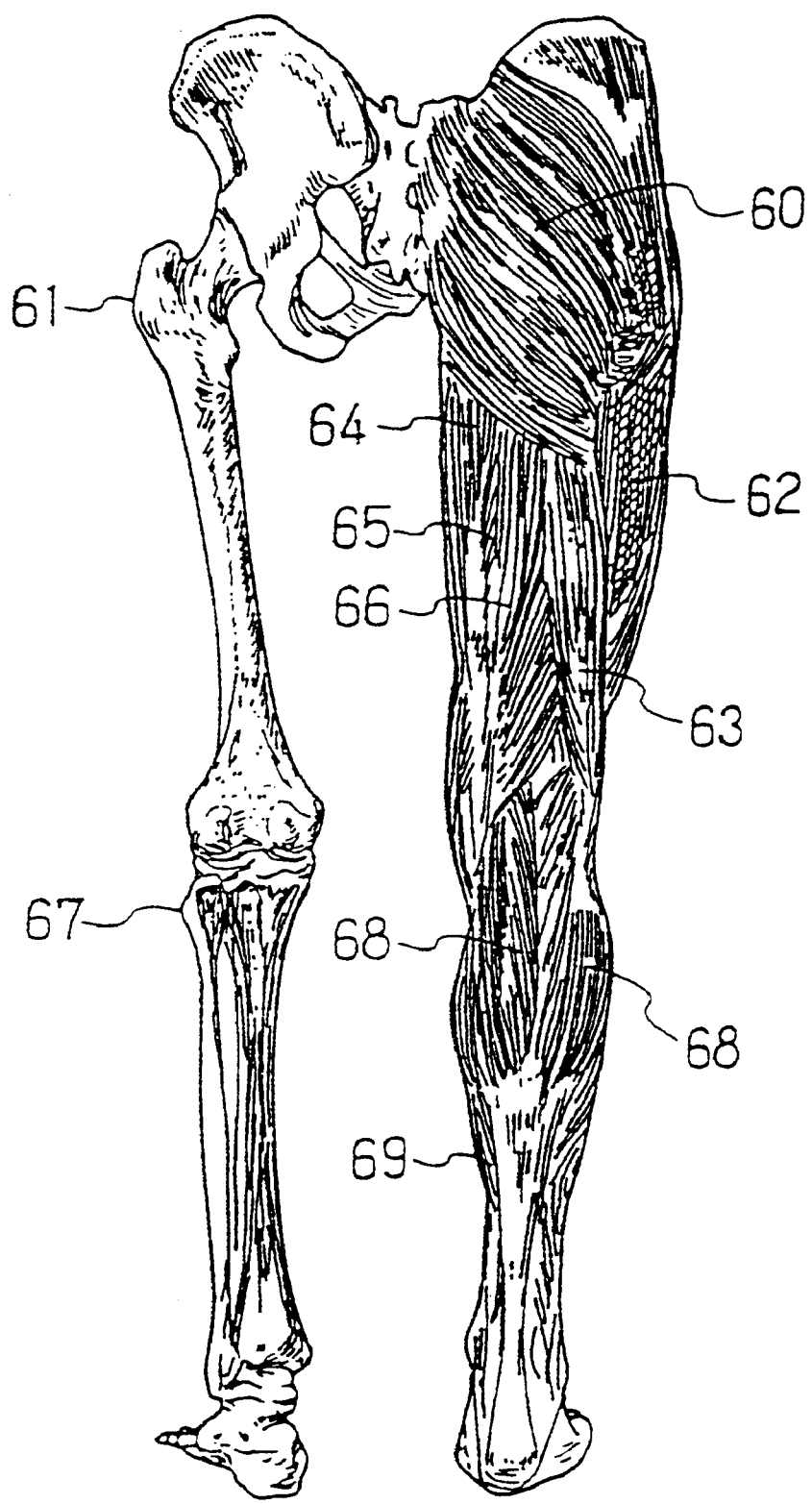
FIG. 39 is a skeleton and partial muscle chart of the leg seen from the back.

FIG. 39 is a skeleton and partial muscle chart of the leg seen from the back.

In FIG. 39, numeral 60 denotes the musculus glutaeus maximus; 61 denotes the trochanter major; 62 denotes the tractus iliotibialis; 63 denotes the musculus biceps femoris; 64 denotes the musculus adductor magnus; 65 denotes musculus semimembranosus; 66 denotes musculus semitendinosus; 67 denotes the caput fibulae; 68 denotes the musculus gastrocnemius; and 69 denotes the musculus soleus.

Figure 40:
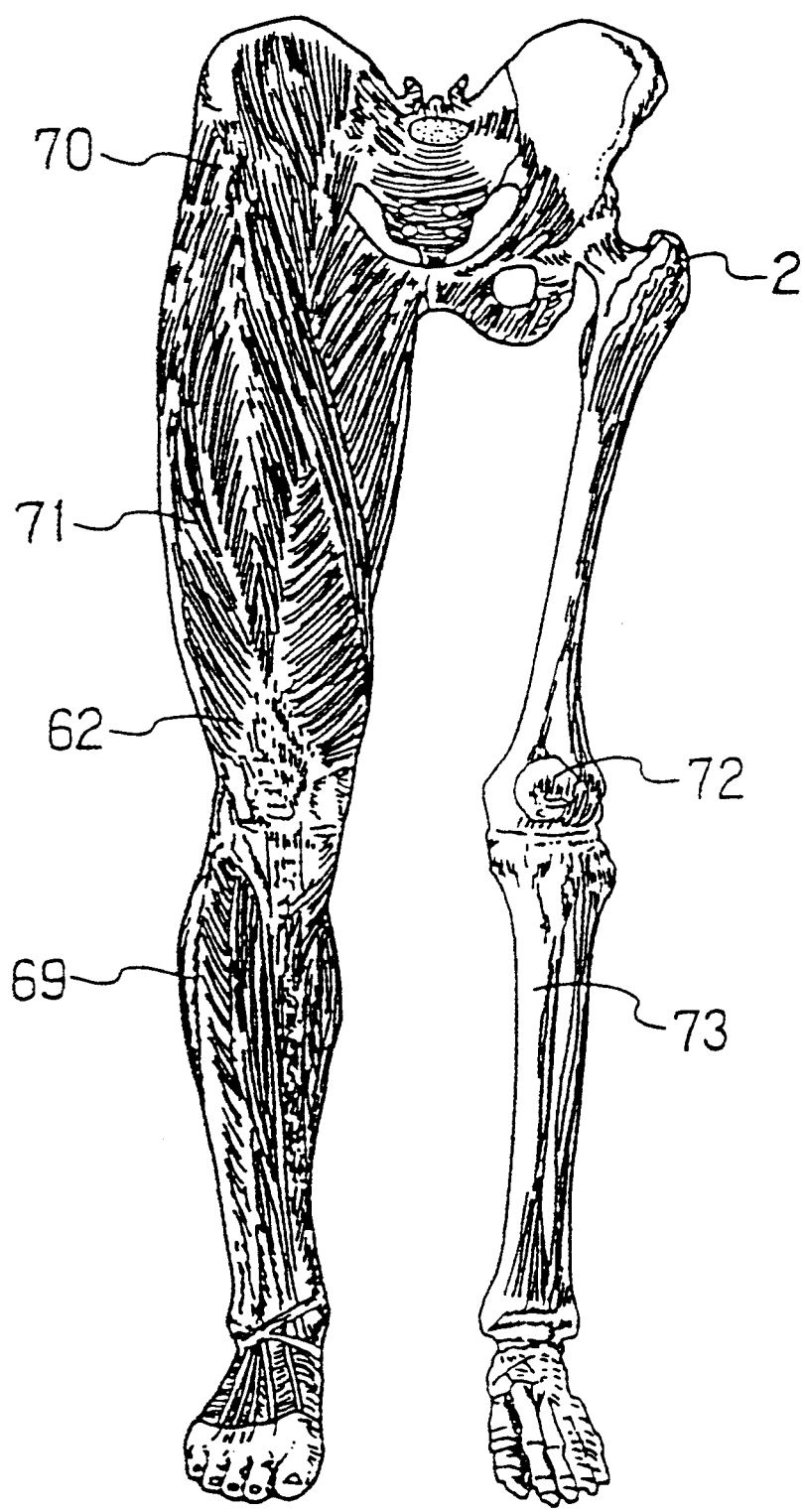
FIG. 40 is a skeleton and partial muscle chart of the leg seen from the front.

Furthermore, FIG. 40 is a skeleton and partial muscle chart of the leg seen from the front side.

In FIG. 40, numeral 70 denotes the musculus tensor fasciae latae; 71 denotes the musculus vastus lateralis; 72 denotes the patella; and 73 denotes the tibia.

Moreover, in the present invention, the wording "in the vicinity of - - - " is used to explain the location of the garment on which the portions having a strong straining force is located. It signifies that some dislocation from the predetermined location is admissible within a scope enabling the achievement of the purposes of the present invention.

In the garment of the present invention, the intended garment can be obtained by using portions having a strong straining force (A), (A'), (B), (B'), etc. singly or in appropriate combinations thereof, and furthermore by applying, if necessary, at least one of (C), (D), (E), etc. However, since there are numerous numbers of such combinations, we show the figures of the representative examples of the leg protection garment of the present invention and will explain them hereinafter. Therefore, the leg protection garment of the present invention is not limited to the garments shown in the figures. Moreover, it is essential for the leg protection garment of the present invention to have a leg portion, and so garments that do not have leg portions, for example, skirts, etc. are not included in the leg protection garment of the present invention. A garment having a lower half of the body part that is applied in close contact with the leg region such as tights (hereinafter, tights will be used for an abbreviation) is included in the garment of the present invention. Moreover, the width of the portion having a strong straining force in the figures is not limited to the width represented in the figures, and can appropriately be modified within a scope not hindering the effects of the present invention. Furthermore, in the figures, in a case where the portion having a strong straining force is divided into two directions or where the portions having a strong straining force are crossing each other, most figures show each portion having a strong straining force individually so as to clarify the effect. However, the contacting place or crossing place of each portion having a strong straining force may be one continuous portion and is not limited to the portion having a strong straining force shown in the figures. Hereinafter, each portion having a strong straining force will be explained with reference to tights.

Figure 1:
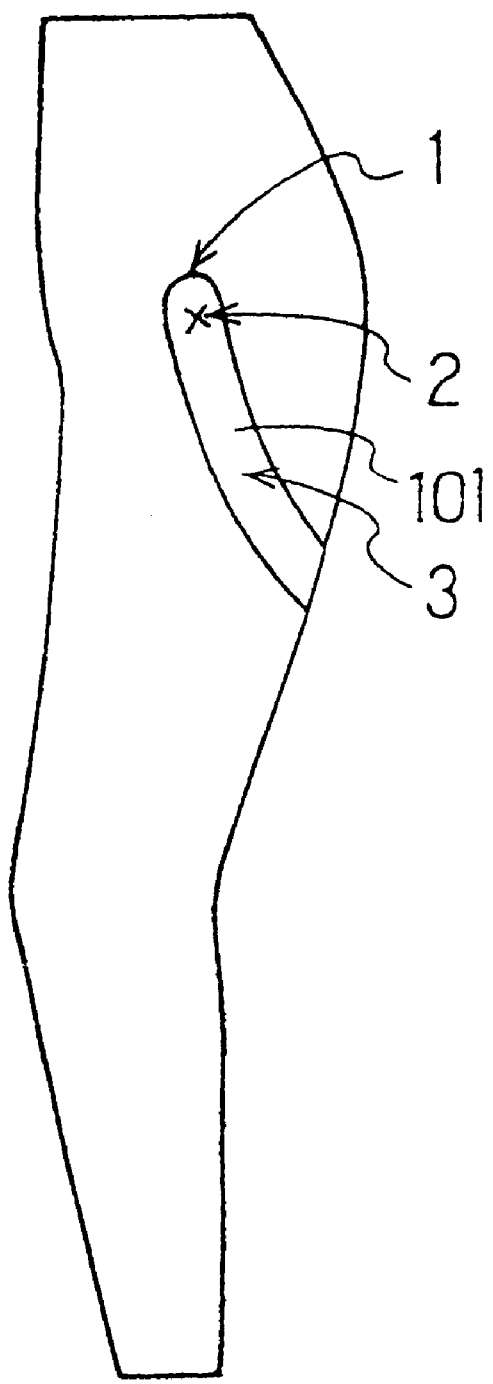
FIG. 1 is a side view of a leg protection garment of the present invention seen from the outside.
Figure 2:
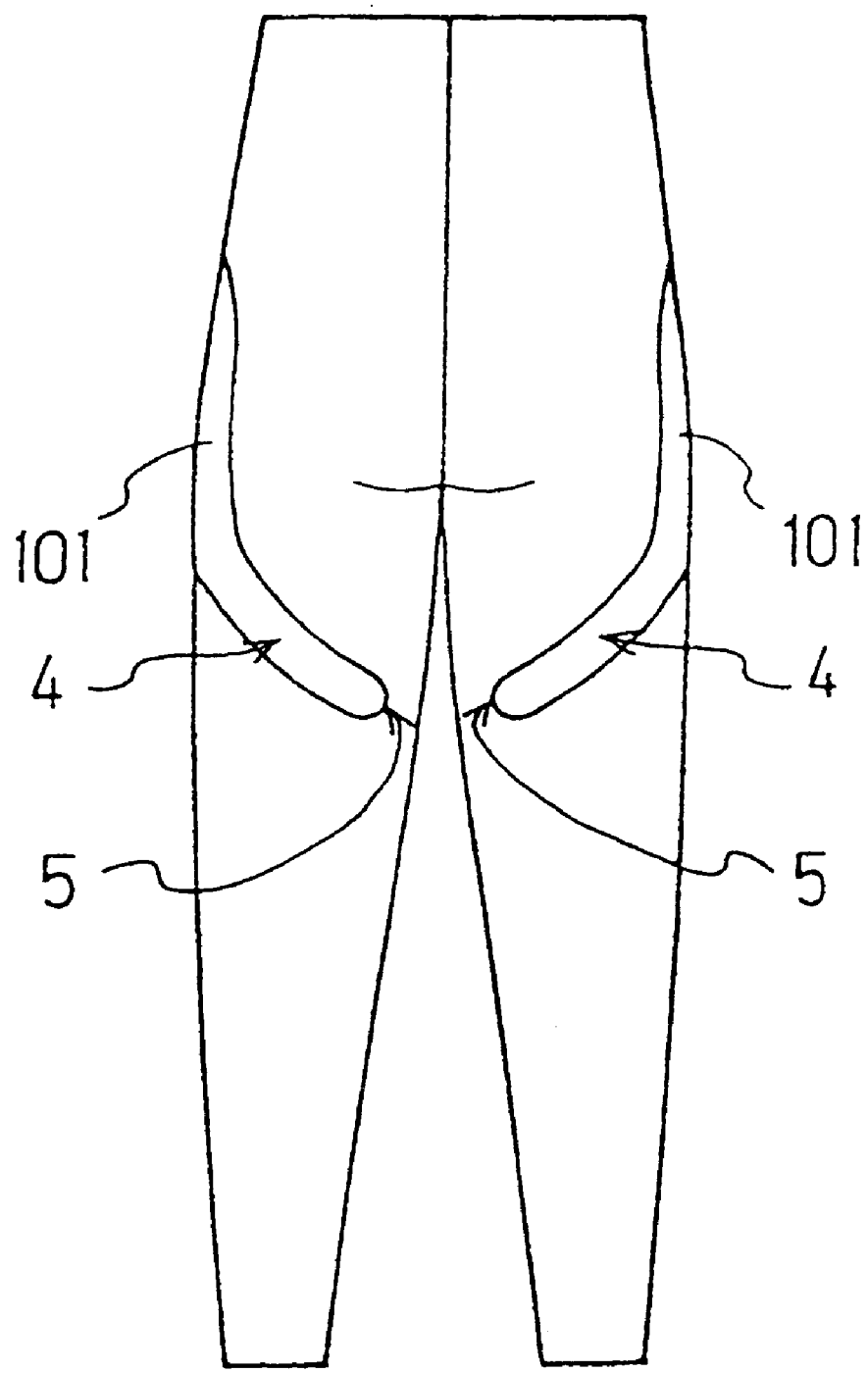
FIG. 2 is a rear view of a leg protection garment of the present invention.
Figure 3:
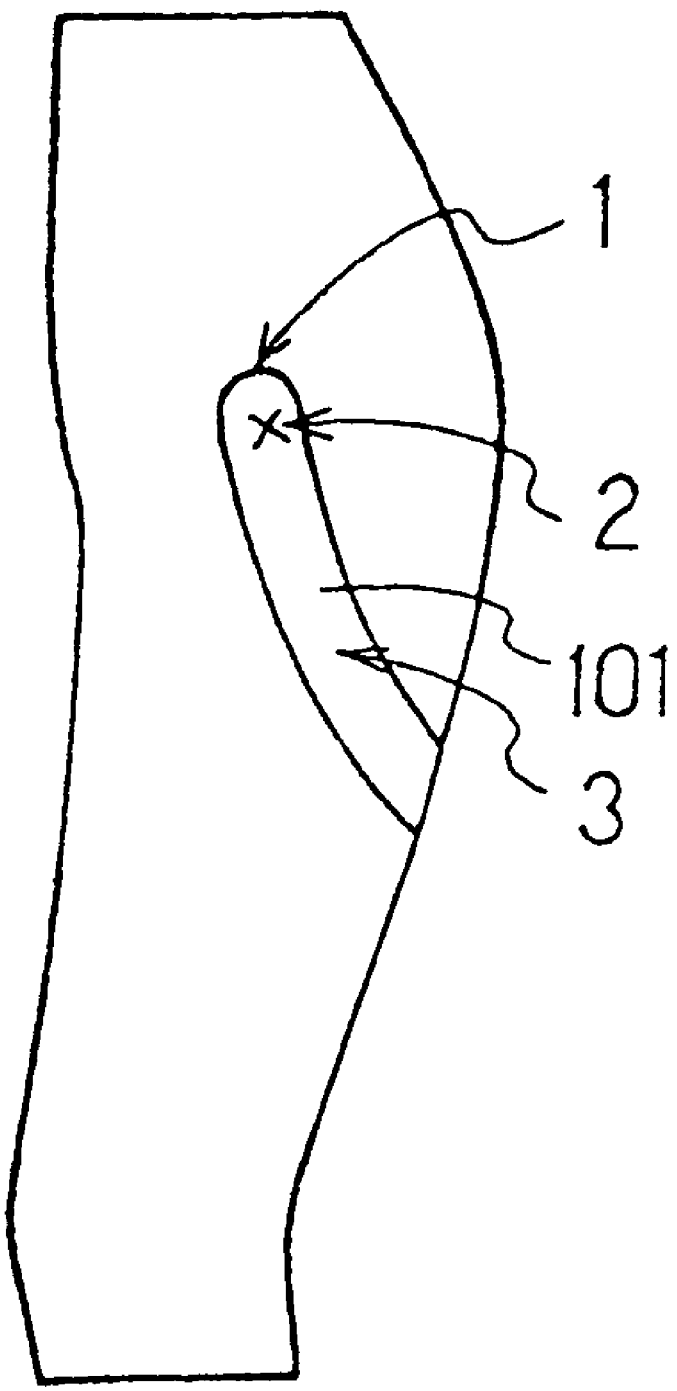
FIG. 3 is a side view of a leg protection garment of the present invention seen from the outside.
Figure 4:
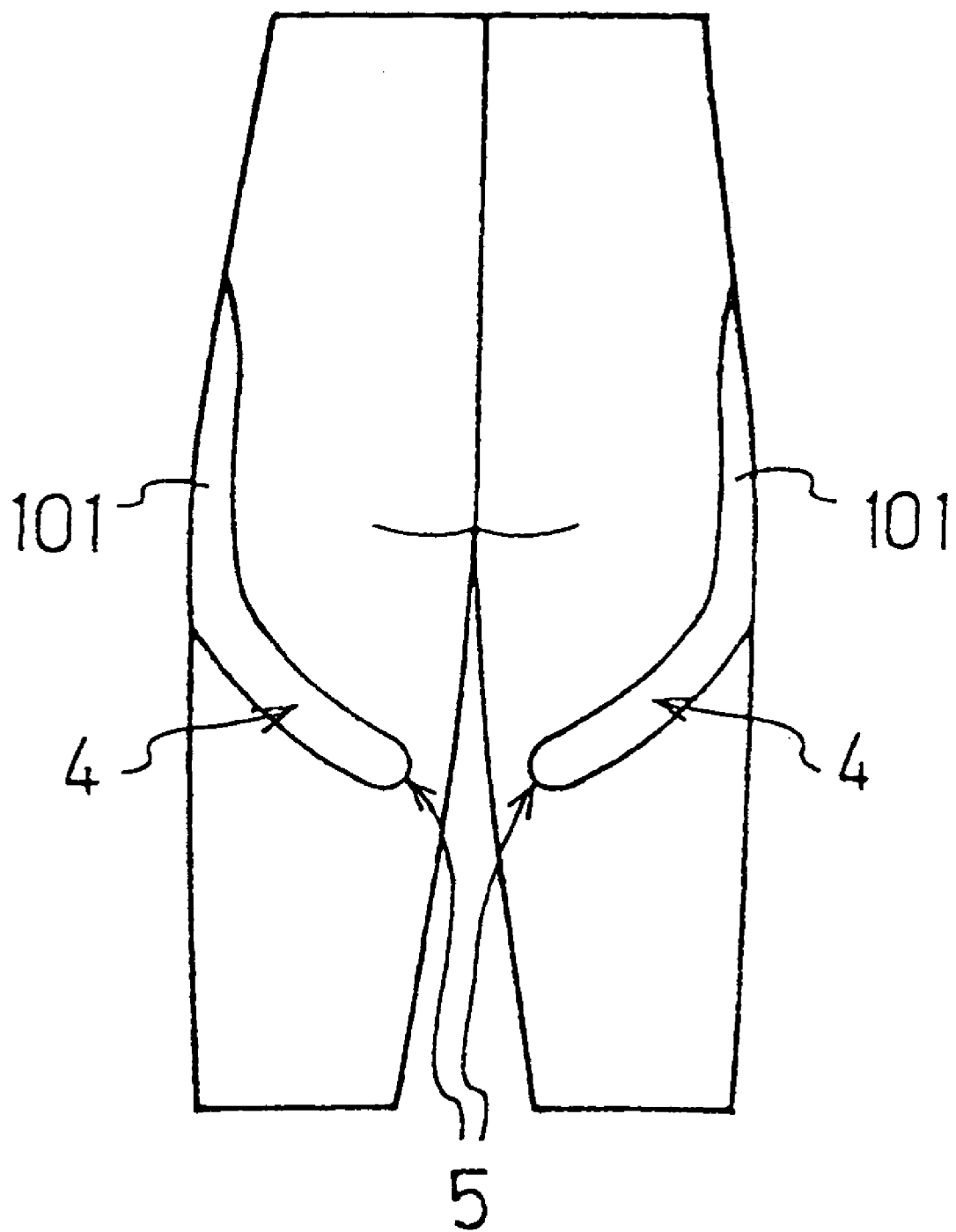
FIG. 4 is a rear view of a leg protection garment of the present invention.

FIGS. 1 to 4 are figures showing a leg protection garment (1) of one embodiment of the present invention for explaining a leg protection garment having only a strong straining force portion 101 (A) as a portion having a strong straining force. FIG. 1 is a side view of ankle length tights seen from the outside; FIG. 2 is a rear view of ankle length tight; FIG. 3 is a side view of tights of below-knee length seen from the outside; and FIG. 4 is a rear view of tights of below-knee length. It is necessary for the leg protection garment of the present invention to have at least a lower half of the body part having a leg portion of a length capable of covering the patella region. Specifically in the case of tights, the length of capable of covering the patella region generally means the length being longer than below-knee length. In the present invention, tights of such length will be explained mainly with reference to ankle length tights as representative examples. However, a shorter length than ankle length, for example, below-knee length may be employed. Moreover, some embodiments of the portion having a strong straining force, for example, an embodiment in which the portion having a strong straining force extends to the vicinity of the ankle, need to be longer than below-knee length.

The portion having a strong straining force 101 (A) will be explained with reference to FIGS. 1 and 2. The portion having a strong straining force 101 ranges from an area 1 above the trochanter major to the vicinity 5 of the upper end of the tibia by way of the trochanter major 2 and further the vicinity 3 over the boundary between the musculus biceps femoris and the tractus iliotibialis so as to support the musculus biceps femoris, wherein the portion obliquely crosses the vicinity 4 of the tendon region located below the muscle belly of the musculus biceps femoris without crossing the muscle belly of the musculus biceps femoris. The effect of supporting the musculus biceps femoris from the side helps the musculus biceps femoris to contract, and in turn to support the flexion of the articulatio genus, the extension of articulatio coxae, and the excycloduction of the articulatio genus at the time of semiflexing the knee. Moreover, the effect of supporting a predetermined muscle, the musculus biceps femoris in this case, is that a massage effect is generated and the flow of blood and lymphocyte is promoted, so that energy consumption or accumulation of lactic acid can be reduced and the recovery from muscle fatigue can be improved. Moreover, since the portion having a strong straining force (A) dose not cross the muscle belly of the musculus biceps femoris, the muscle contraction is not inhibited.

Figure 7:
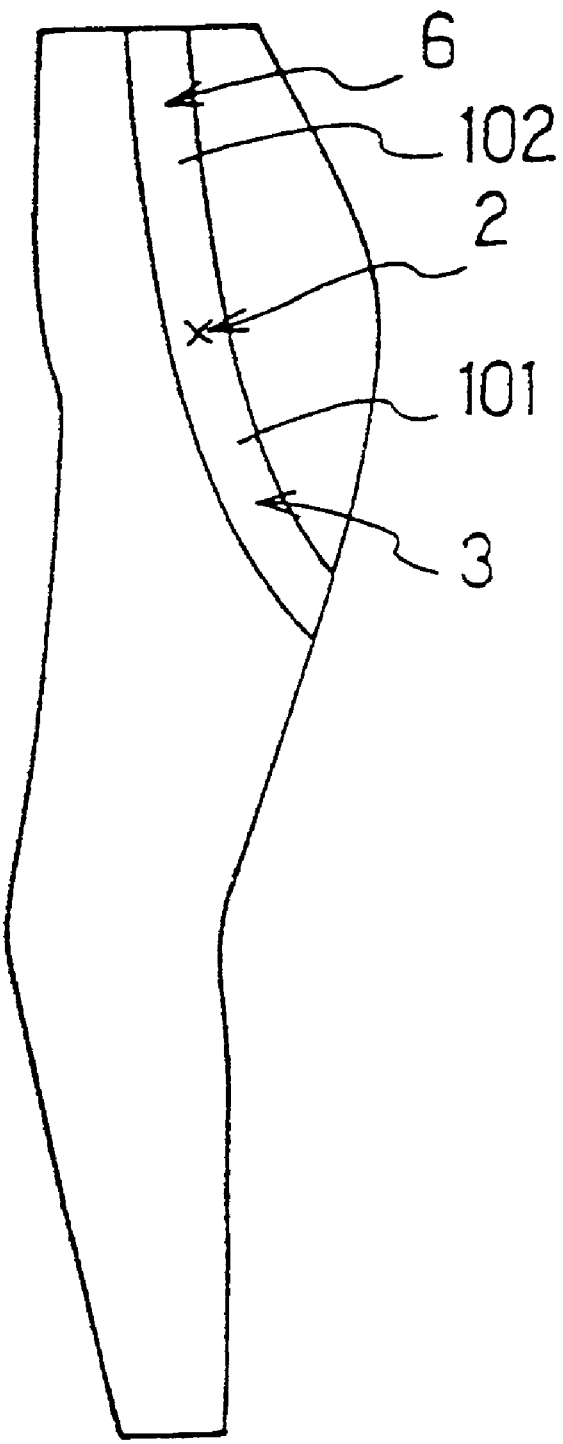
FIG. 7 is a side view of a leg protection garment of the present invention seen from the outside.

FIG. 7 is a side view of a leg protection garment (1) of one embodiment of the present invention seen from the outside for explaining that the above mentioned portion having a strong straining force 101 (A) further has a portion having a strong straining force 102 that passes the portion 6 over the musculus tensor fasciae latae in an area above the trochanter major.

Moreover, as shown in FIG. 7, it is preferable that the portion having a strong straining force 101 (A) has the portion having a strong straining force 102 that passes the portion 6 over the musculus tensor fasciae latae in an area above the trochanter major. The musculus tensor fasciae latae is a muscle that passes over the trochanter major and plays a role in preventing the trochanter major from dislocating. Therefore, in addition to the above mentioned effect, the portion having a strong straining force has an effect of strengthening the trochanter major by supporting the musculus tensor fasciae latae from the upside.

Figure 8:
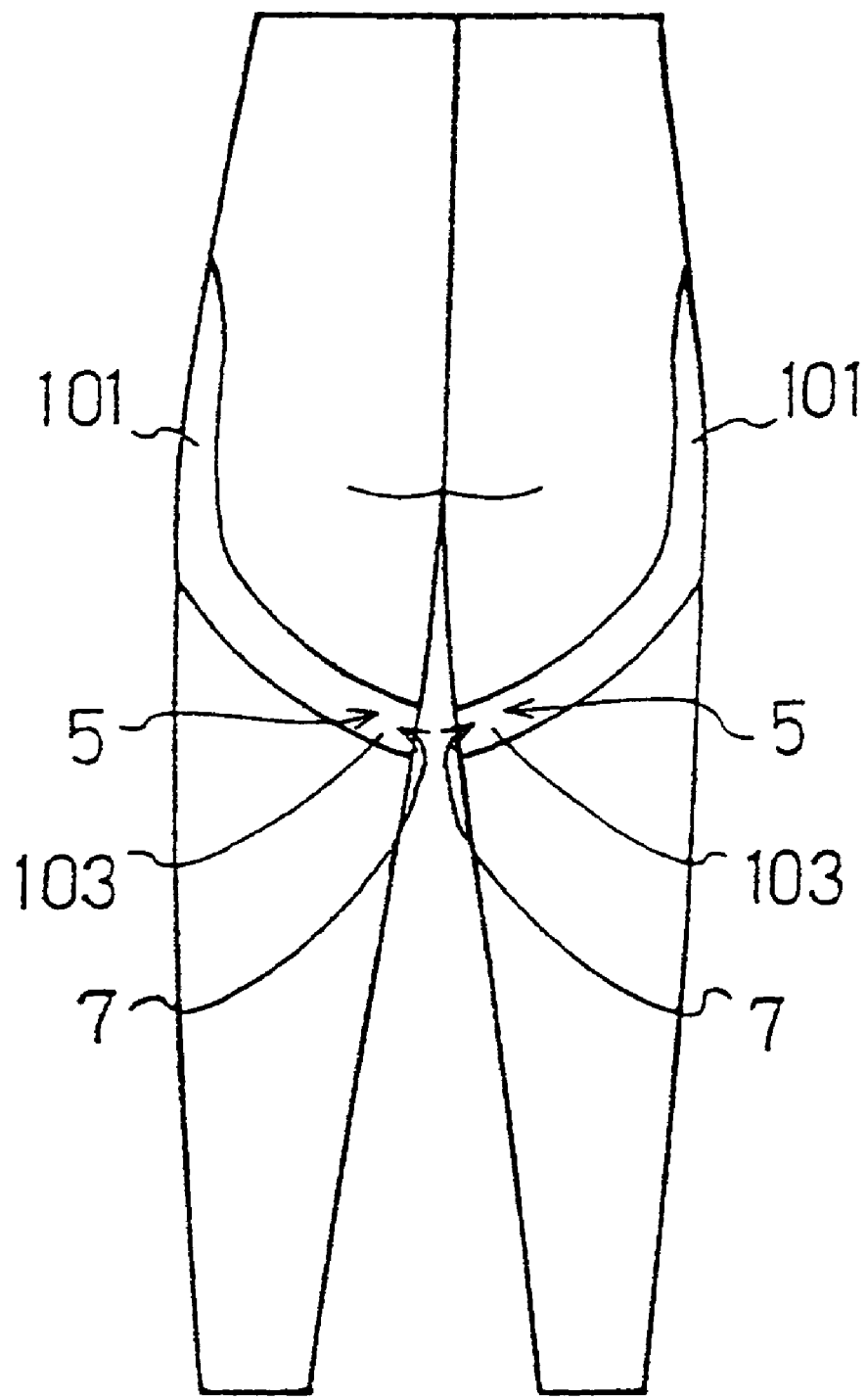
FIG. 8 is a rear view of a leg protection garment of the present invention.

FIG. 8 is a rear view showing a leg protection garment (1) of one embodiment of the present invention for explaining that the above mentioned portion having a strong straining force 101 (A) has a portion having a strong straining force 103 that ranges from the vicinity 5 of the upper end of the fibula to the vicinity 7 of the attaching region of the musculus semitendinosus and the musculus semimembranosus.

Moreover, as shown in FIG. 8, it is preferable that the portion having a strong straining force 101 (A) has the portion having the strong straining force 103 which further ranges from the vicinity 5 of the upper end of the fibula to the vicinity 7 of the attaching region of the musculus semitendinosus and the musculus semimembranosus. The effect is, by extending the portion having a strong straining force 101 (A) shown in FIGS. 1 and 2, to further increase the effect of supporting the musculus biceps femoris, the same effect as that of the portion having a strong straining force 101 (A). Moreover, the effect of supporting the musculus biceps femoris is improved. From the viewpoint of wearing comfort, however, one having only the above mentioned portion having a strong straining force 101 (A) which does not extend to the vicinity 7 over the attaching region of the musculus semitendinosus and the musculus semimembranosus, is more excellent.

Figure 5:
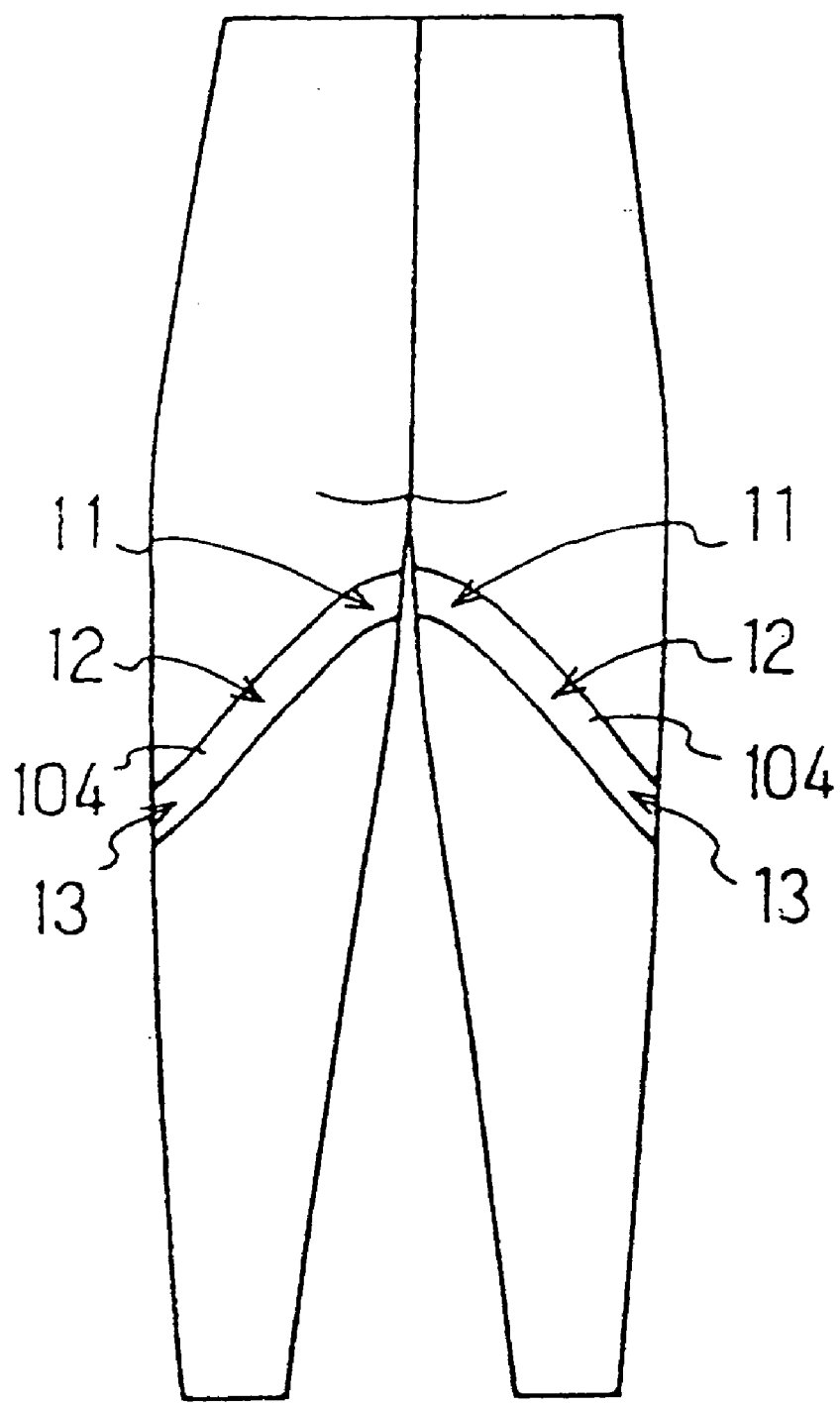
FIG. 5 is a rear view of a leg protection garment of the present invention.
Figure 6:
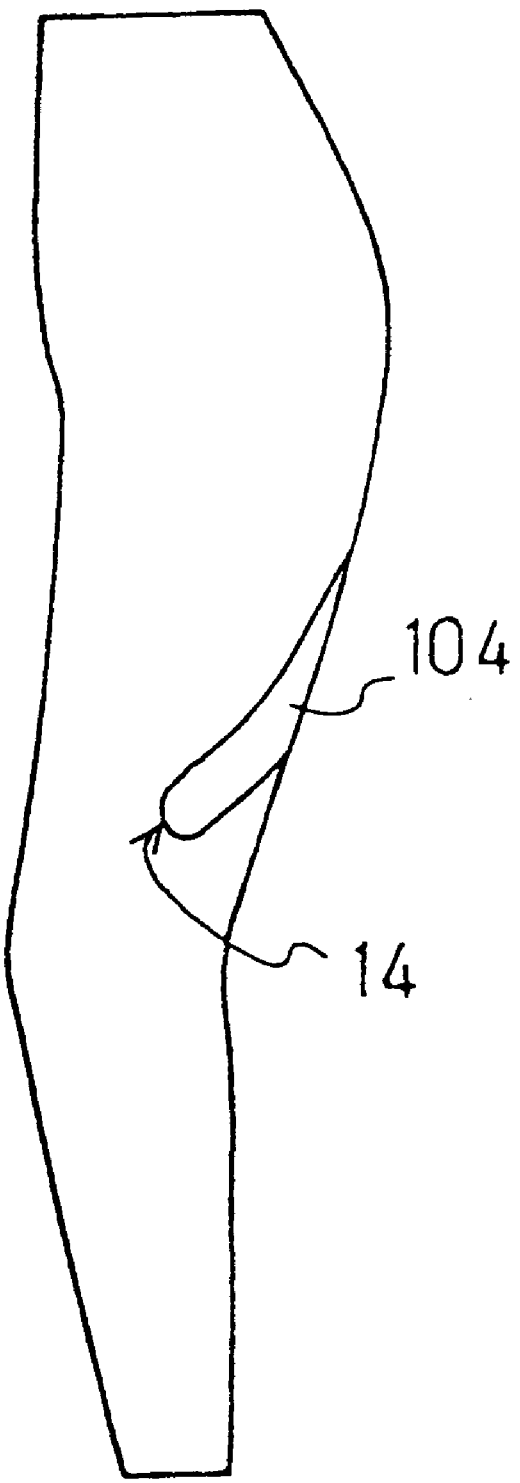
FIG. 6 is a side view of a leg protection garment of the present invention seen from the outside.

FIGS. 5 and 6 are figures showing a leg protection garment (1) of one embodiment of the present invention for explaining the leg protection garment having only a portion having a strong straining force 104 (B) as a portion having a strong straining force. FIG. 5 is a rear view of tights, and FIG. 6 is a side view of a tights seen from the outside, respectively.

The portion having a strong straining force 104 (B) will be explained with reference to FIGS. 5 and 6. The portion having a strong straining force 104 that ranges from an area above the musculus semimembranosus 11 to the vicinity 14 of the upper end of the fibula by way of the vicinity 12 over the boundary between the musculus semimembranosus and the musculus adductor magnus so as to support the musculus semitendinosus and the musculus semimembranosus, wherein the portion obliquely crosses the vicinity 13 of the tendon region located below the muscle belly of both the musculus semitendinosus and the musculus semimembranosus without crossing the muscle belly of the musculus semitendinosus and the musculus semimembranosus. The effect is, by supporting the musculus semitendinosus and the musculus semimembranosus from the side by the portion having a strong straining force, to help the musculus semitendinosus and the musculus semimembranosus to contract. As a result, by supporting the musculus semitendinosus, the flexion of the articulatio genus, the extension of the articulatio coxae, and an intorsion of the lower leg at the time of semiflexing, the knees are supported. Moreover, the effect of the support of the musculus semitendinosus and the musculus semimembranosus is the same as that of the musculus biceps femoris in the above mentioned portion having a strong straining force (A).

Figure 9:
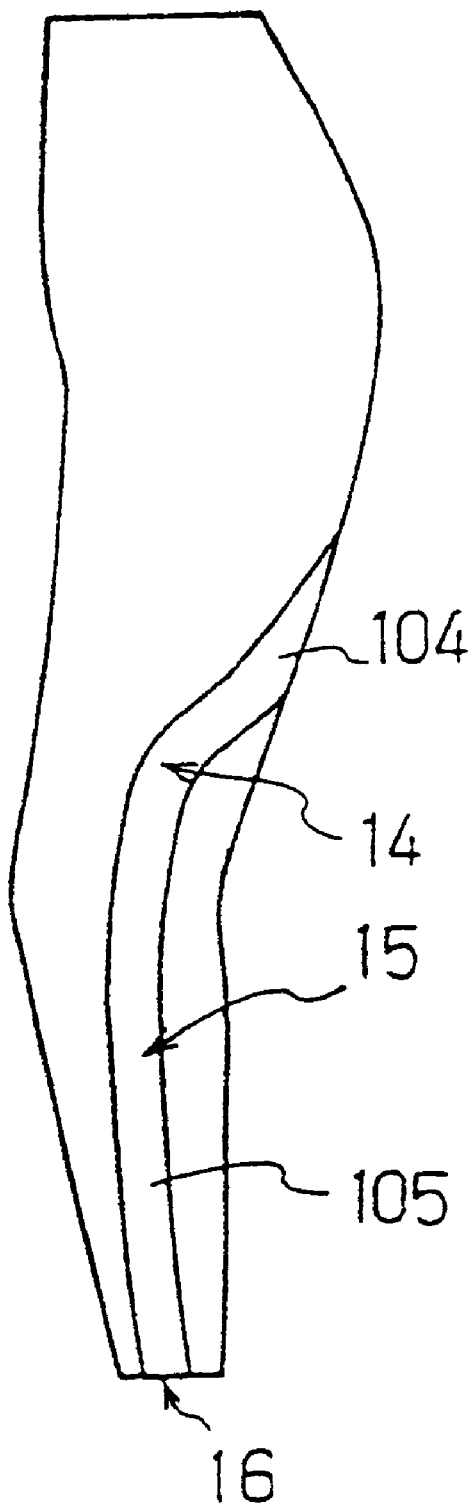
FIG. 9 is a side view of a leg protection garment of the present invention seen from the outside.

FIG. 9 is a side view showing a leg protection garment (1) of one embodiment of the present invention for explaining the leg protection garment in which the above mentioned portion having a strong straining force 104 (B) further has a portion having a strong straining force 105 that ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Moreover, as shown in FIG. 9, it is preferable that the portion having a strong straining force 104 (B) further has the portion having a strong straining force 105 that ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus. The effect is to support the musculus gastrocnemius and the musculus soleus.

Figure 10:
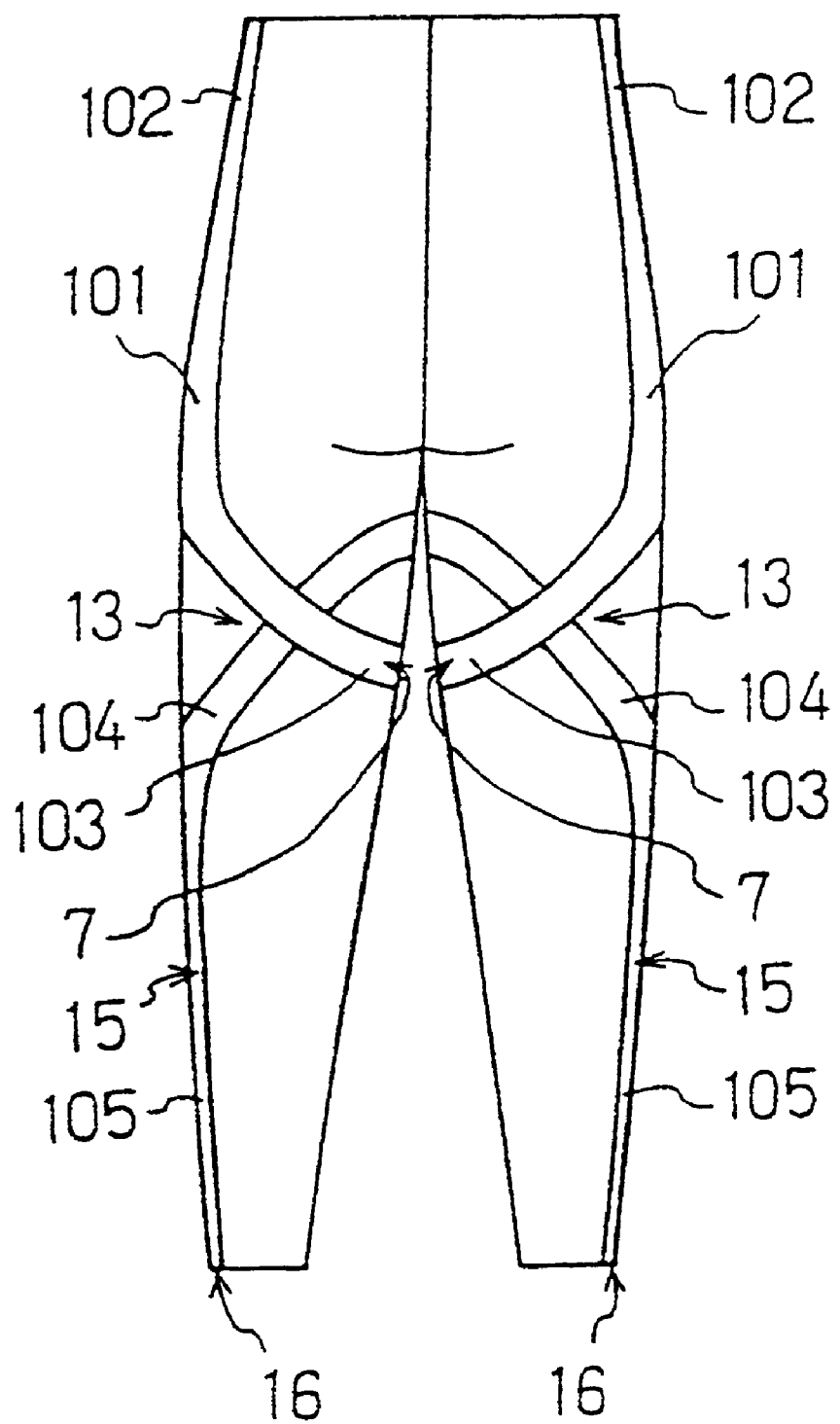
FIG. 10 is a rear view of a leg protection garment of the present invention.
Figure 11:
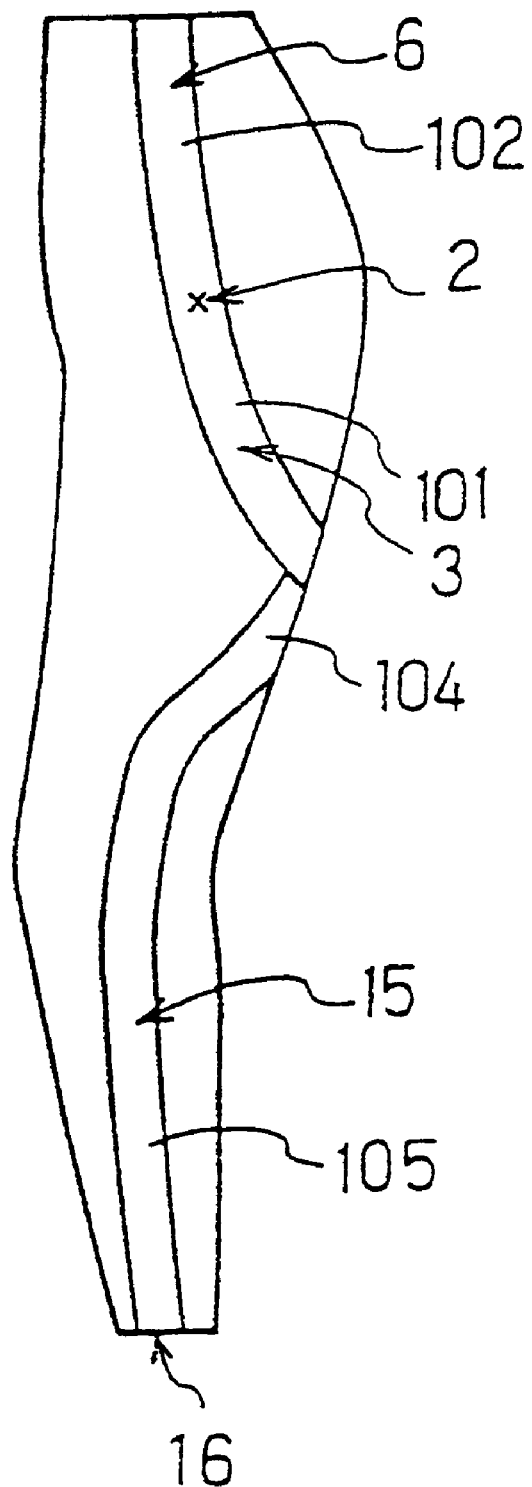
FIG. 11 is a side view of a leg protection garment of the present invention seen from the outside.

FIGS. 10 and 11 are figures showing a leg protection garment (1) of one embodiment of the present invention for explaining the leg protection garment having the portions having a strong straining force 101 (A) and 104 (B) as the portion having a strong straining force. FIG. 10 is a rear view of tights, and FIG. 11 is a side view of tights seen from the outside, respectively. The leg protection garment of an embodiment combining the portions having a strong straining force (A) and (B) has an effect of combining both the support of the musculus biceps femoris by the portion having a strong straining force (A) and the support of the musculus semitendinosus and the musculus semimembranosus by the portion having a strong straining force (B).

Figure 12:
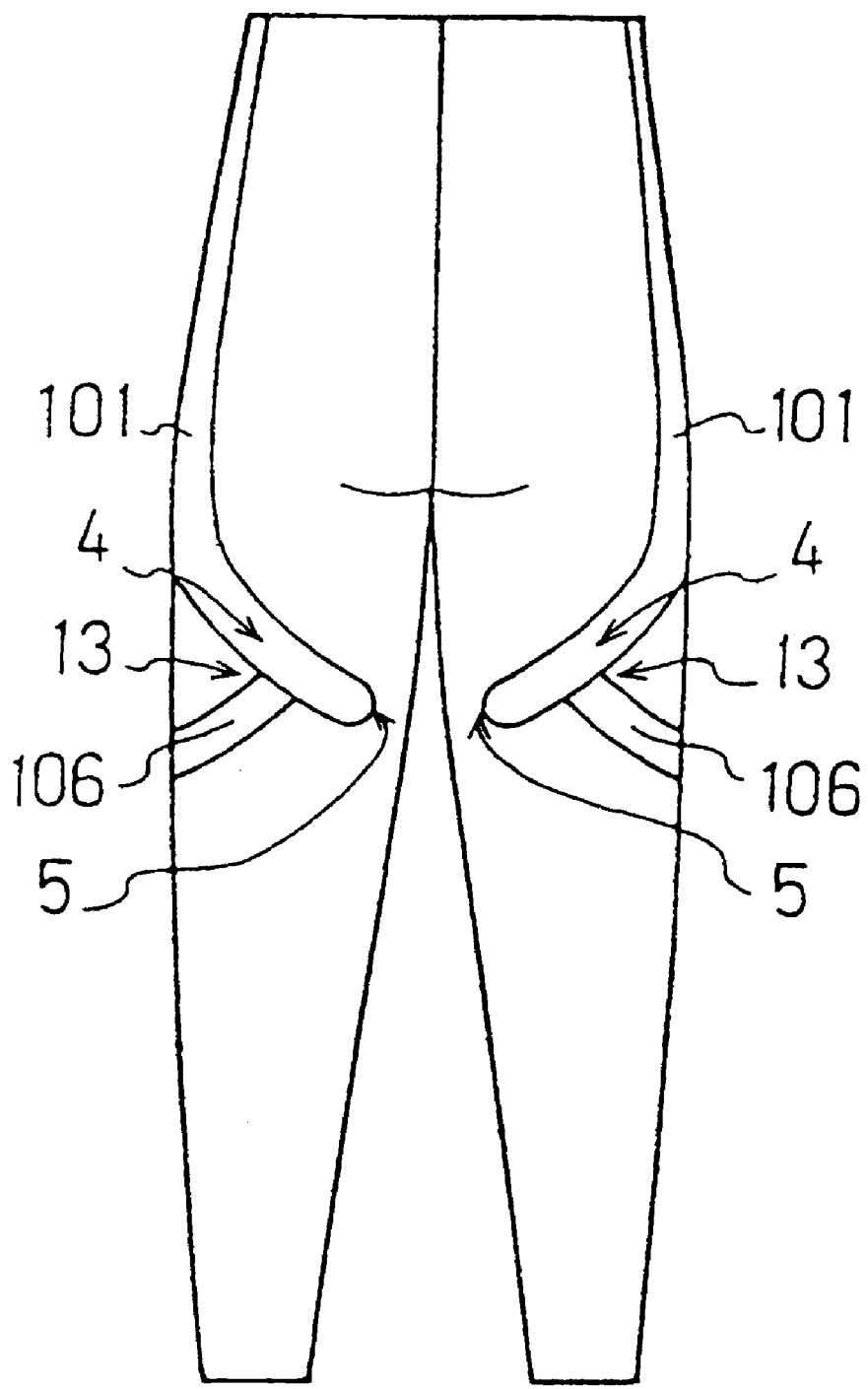
FIG. 12 is a rear view of a leg protection garment of the present invention.
Figure 13:
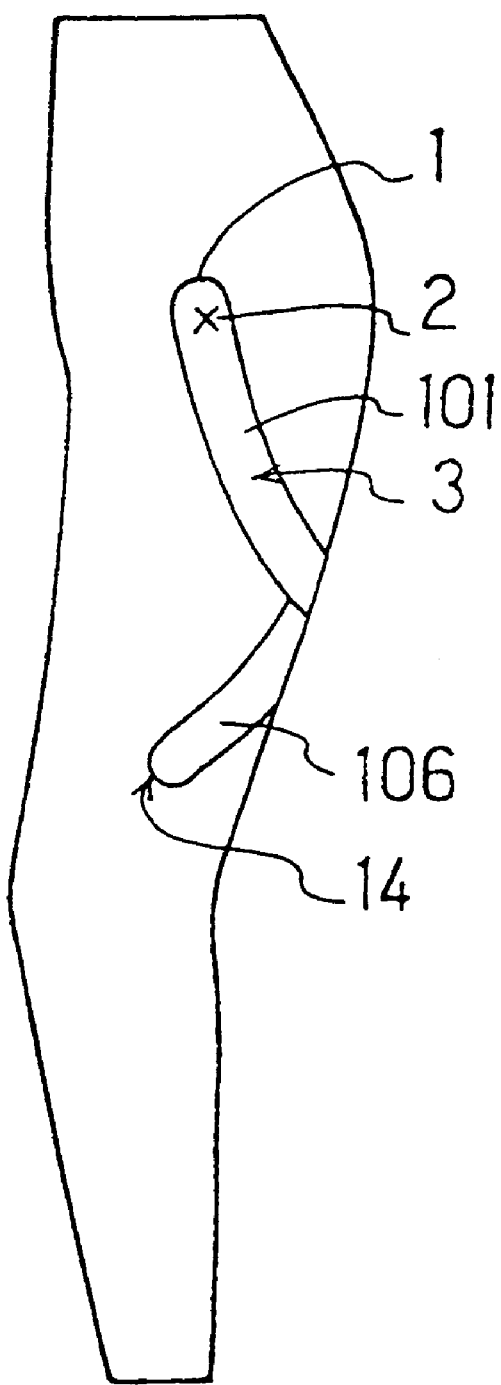
FIG. 13 is a side view of a leg protection garment of the present invention seen from the outside.

FIGS. 12 and 13 are figures showing a leg protection garment (2) of one embodiment of the present invention for explaining a leg protection garment having portions having a strong straining force 101 (A) and 106 (B') as the portion having a strong straining force. FIG. 12 is a rear view of tights, and FIG. 13 is a side view of tights seen from the outside, respectively.

The portion having a strong straining force 106 (B') will be explained with reference to FIG. 12. The portion having a strong straining force 106 (B') ranges from the vicinity 13 of the tendon region located below the muscle bellies of both the musculus semitendinosus and musculus semimembranosus (namely, the crossing place to the portion having a strong straining force 101 (A)) to the vicinity 14 of the fibula, and is a part of the portion having a strong straining force 104 (B).

The effect of the above mentioned leg protection garment is mainly to support the musculus biceps femoris by the portion having a strong straining force (A), and also to support the musculus semitendinosus and the musculus semimembranosus by the portion having a strong straining force (B').

Figure 14:
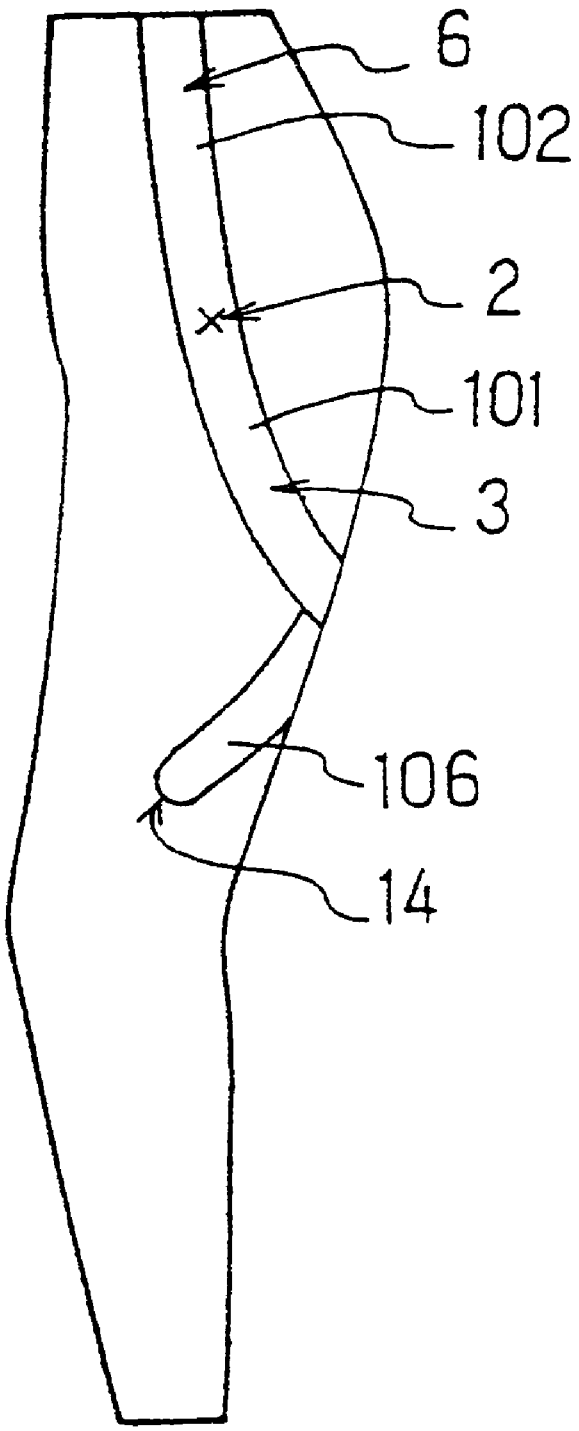
FIG. 14 is a side view of a leg protection garment of the present invention seen from the outside.

FIG. 14 is a side view showing a leg protection garment (2) of one embodiment of the present invention for explaining a leg protection garment in which the portion having a strong straining force 101 (A) of the leg protection garment according to FIGS. 12 and 13 further has the portion having a strong straining force 102 that passes the portion 6 over the musculus tensor fasciae latae in an area above the trochanter major.

Figure 15:
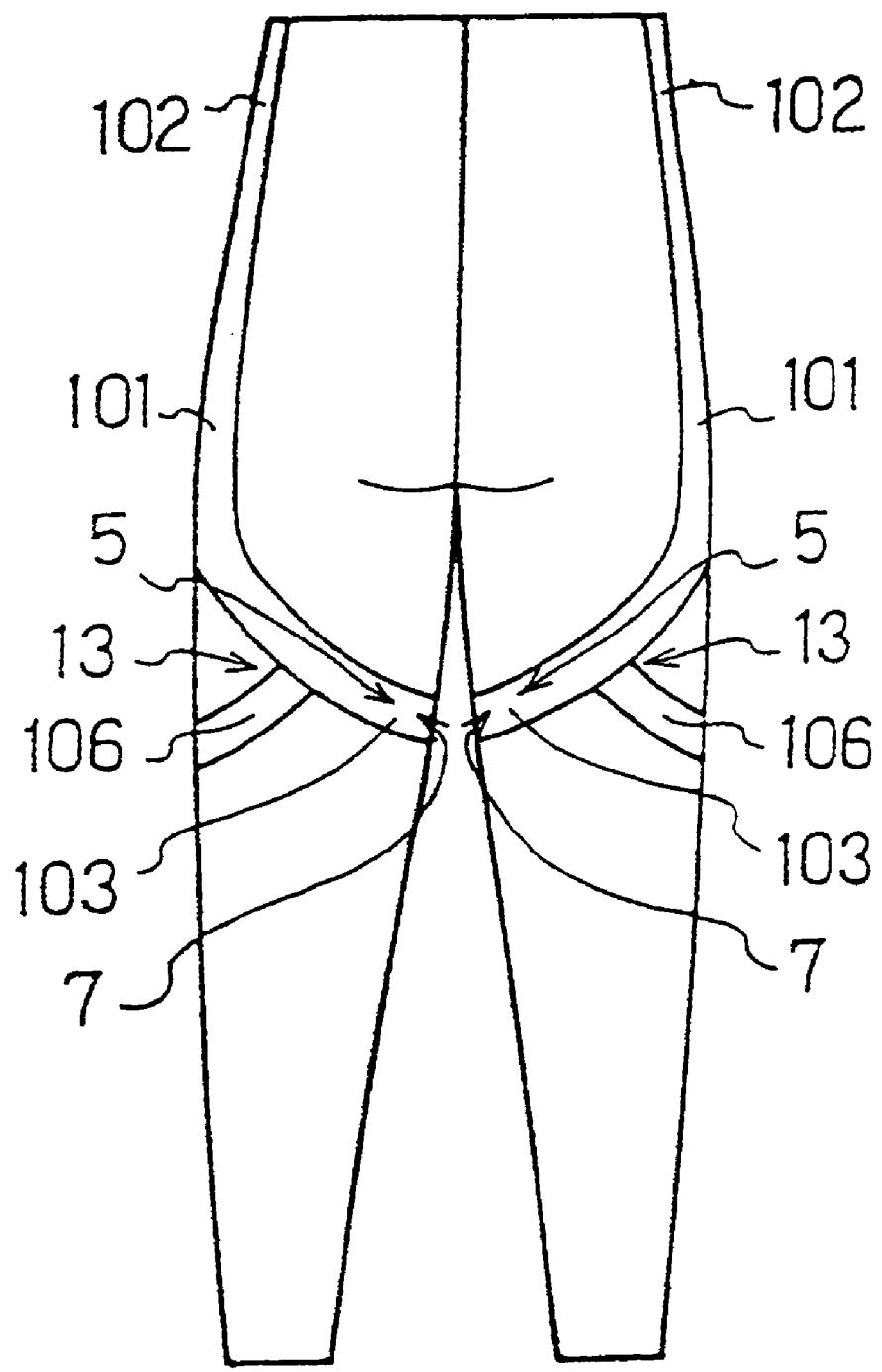
FIG. 15 is a rear view of a leg protection garment of the present invention.

FIG. 15 is a rear view showing a leg protection garment (2) of one embodiment of the present invention for explaining the leg protection garment in which the portion having a strong straining force 101 (A) of the leg protection garment according to FIG. 14 further has a portion having the strong straining force 103 that ranges from the vicinity 5 of the upper end of the fibula to the vicinity 7 over the attaching region of the musculus semitendinosus and the musculus semimembranosus.

Figure 16:
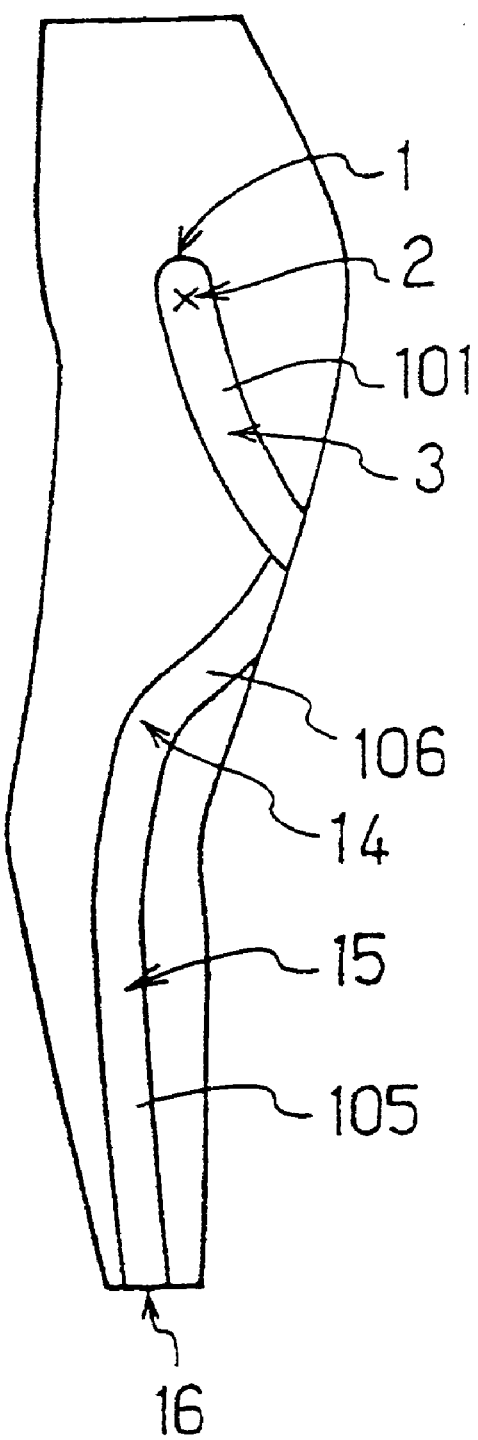
FIG. 16 is a side view of a leg protection garment of the present invention seen from the outside.

FIG. 16 is a side view showing a leg protection garment (2) of one embodiment of the present invention seen from the outside for explaining the leg protection garment in which the portion having a strong straining force 106 (B') of the leg protection garment according to FIGS. 12 and 13 further has a portion having a strong straining force 105 that ranges from the vicinity 14 of the upper end of the fibula to the vicinity 16 of the upper region of the ankle by way of the vicinity 15 over the boundary between the musculus gastrocnemius and the musculus soleus so as to support the musculus gastrocnemius and the musculus soleus.

Figure 17:
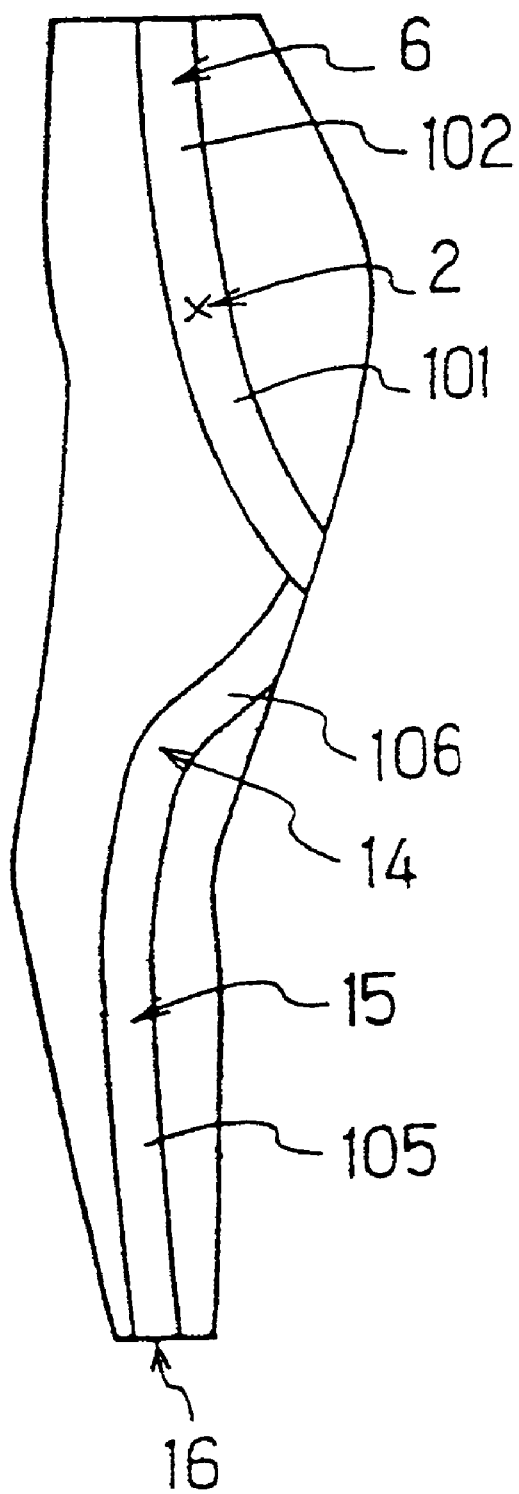
FIG. 17 is a side view of a leg protection garment of the present invention seen from the outside.

FIG. 17 is a side view showing a leg protection garment (2) of one embodiment of the present invention seen from the outside for explaining a leg protection garment in which the portion having a strong straining force 106 (B') of the leg protection garment according to FIG. 15 further has the portion having a strong straining force 105 that ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Moreover, as shown in FIGS. 14 to 17, it is preferable for the same reason as in the above mentioned leg protection garment (1) that the portion having a strong straining force 101 (A) has, in an area above the trochanter major, the portion having a strong straining force 102 that passes the portion 6 over the musculus tensor fasciae latae; the portion having a strong straining force 101 (A) further has the portion having a strong straining force 103 that ranges from the vicinity 5 of the upper region of the tibia to the vicinity 7 over the attaching region of the musculus semitendinosus and the musculus semimembranosus; and the portion having a strong straining force 106 (B') has the portion having a strong straining force 105 that ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Figure 18:
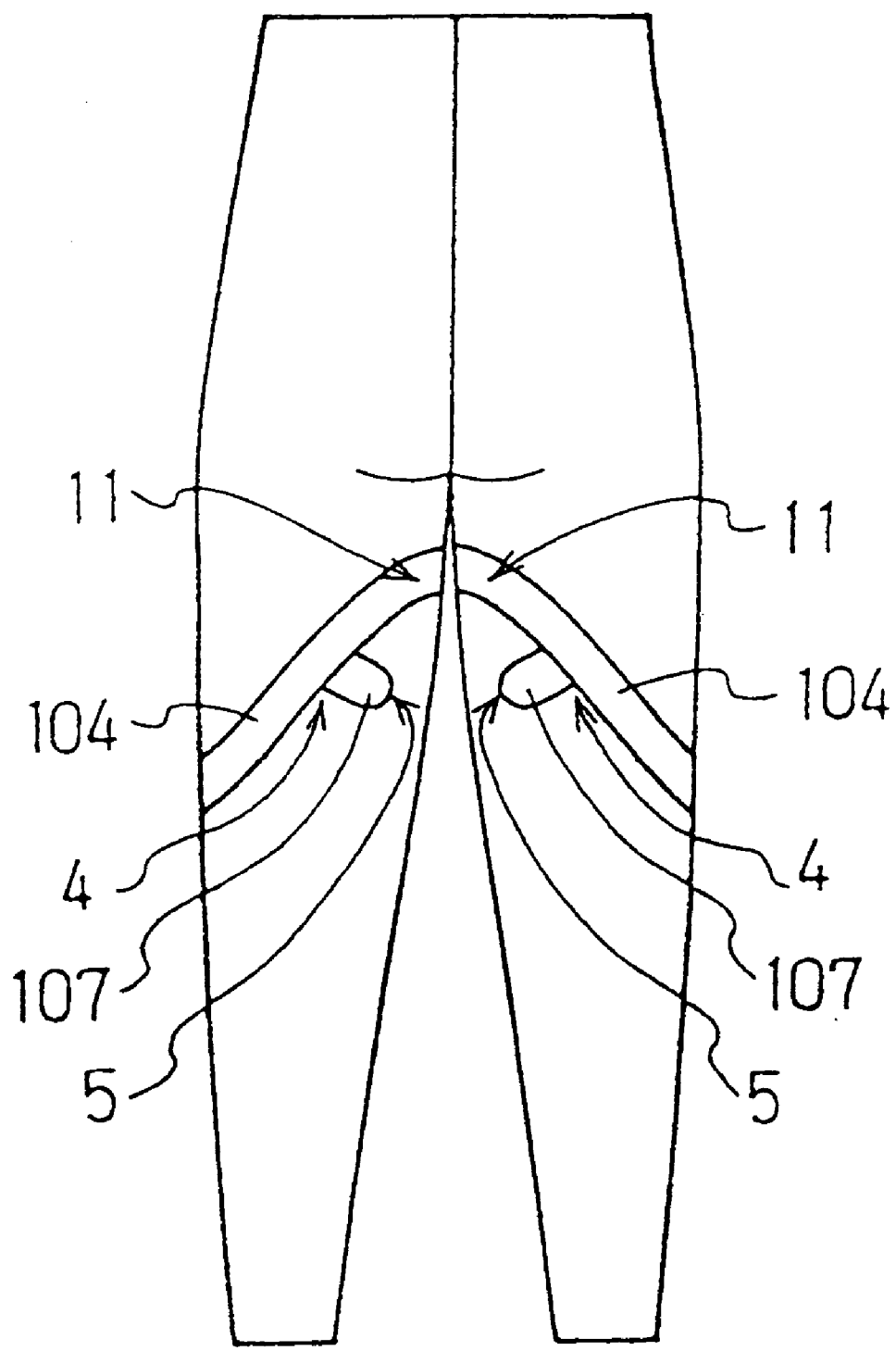
FIG. 18 is a rear view of a leg protection garment of the present invention.
Figure 19:
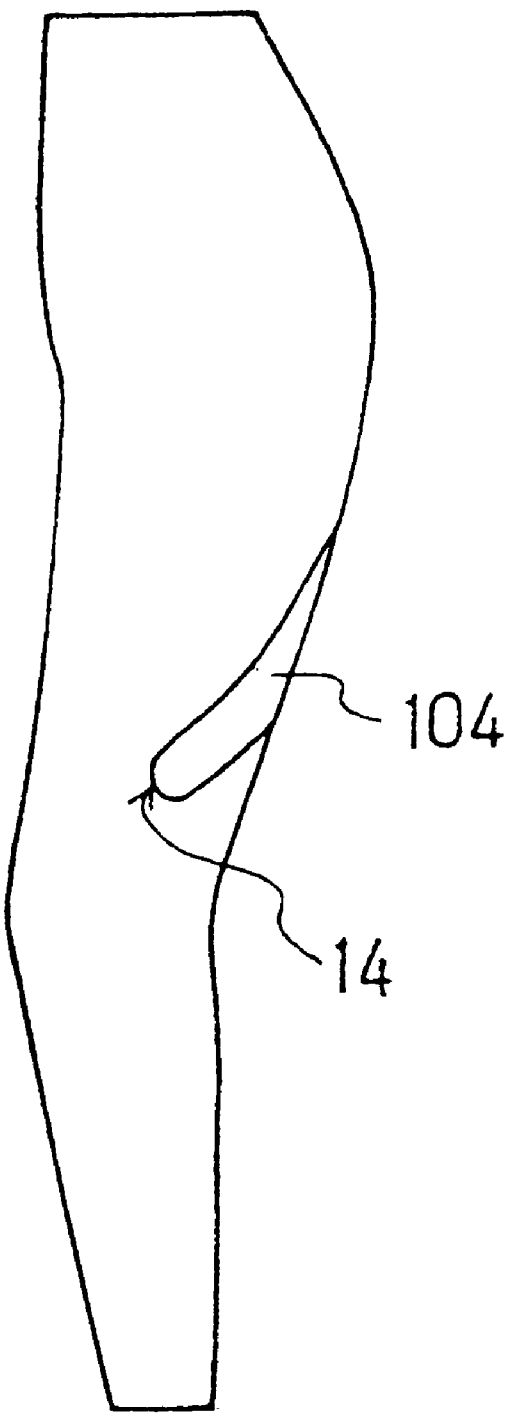
FIG. 19 is a side view of a leg protection garment of the present invention seen from the outside.

FIGS. 18 and 19 are views showing a leg protection garment (3) of one embodiment of the present invention for explaining a leg protection garment having the portion having a strong straining force 107 (A') and 104 (B) as the portion having a strong straining force. FIG. 18 is a rear view of tights, and FIG. 19 is a side view of tights seen from the outside, respectively.

The portion having a strong straining force 107 (A') will be explained with reference to FIG. 18. The portion having a strong straining force 107 (A') ranges from the vicinity 4 of the tendon region located below the muscle belly of the musculus biceps femoris (namely, the portion crossing to the portion having a strong straining force 104 (B)) to the vicinity 5 of the upper end of the tibia, and is a part of the portion having a strong straining force 101 (A).

The effect of the above mentioned leg protection garment is mainly to support the musculus semitendinosus and musculus semimembranosus by the portion having a strong straining force 104 (B) and also to support the musculus biceps femoris by the portion having a strong straining force 107 (A').

Figure 20:
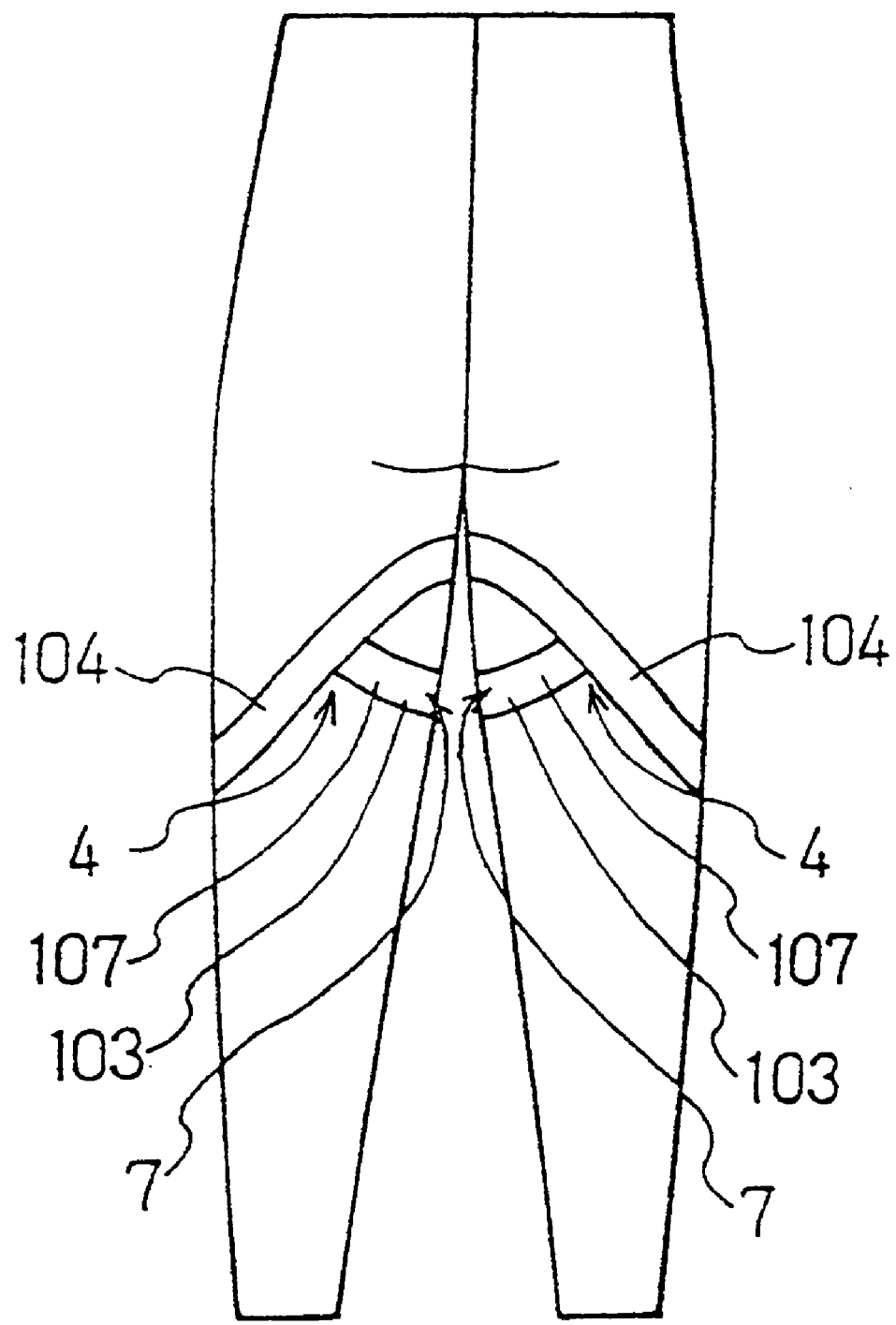
FIG. 20 is a rear view of a leg protection garment of the present invention.
Figure 21:
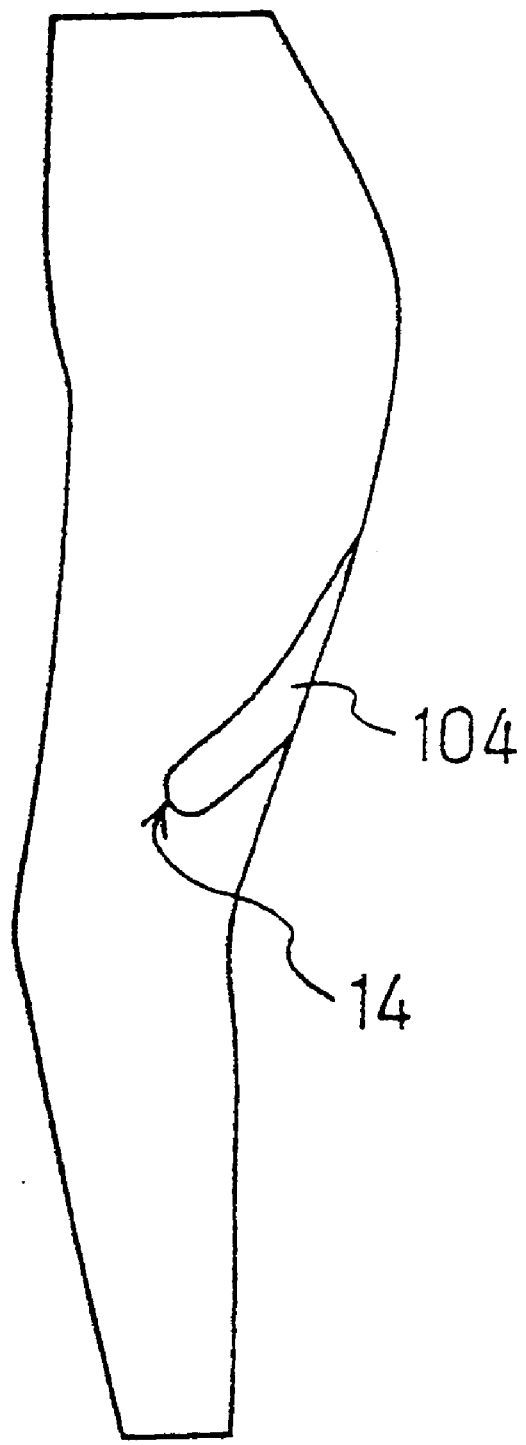
FIG. 21 is a side view of a leg protection garment of the present invention seen from the outside.

FIGS. 20 and 21 are views showing a leg protection garment (3) of one embodiment of the present invention for explaining a leg protection garment in which the portion having a strong straining force 107(A') of the leg protection garment according to FIGS. 18 and 19 further has the portion having a strong straining force 103 that ranges from the vicinity 5 of the upper end of the tibia to the vicinity 7 over the attaching region of the musculus semitendinosus and the musculus semimembranosus. FIG. 20 is a rear view, and FIG. 21 is a side view seen from the outside, respectively.

Figure 22:
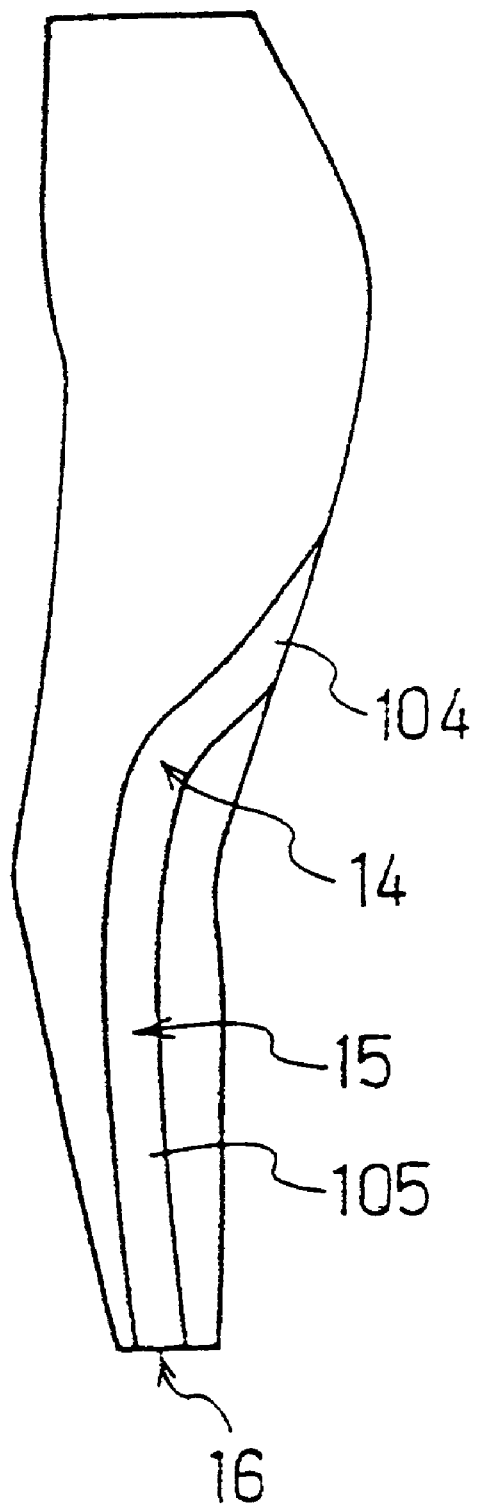
FIG. 22 is a side view of a leg protection garment of the present invention seen from the outside.

FIG. 22 is a side view showing a leg protection garment (3) of one embodiment of the present invention seen from the outside for explaining a leg protection garment in which the portion having a strong straining force 104 (B) in the leg protection garment according to FIGS. 18 and 19 further has the portion having a strong straining force 105 which ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Figure 23:
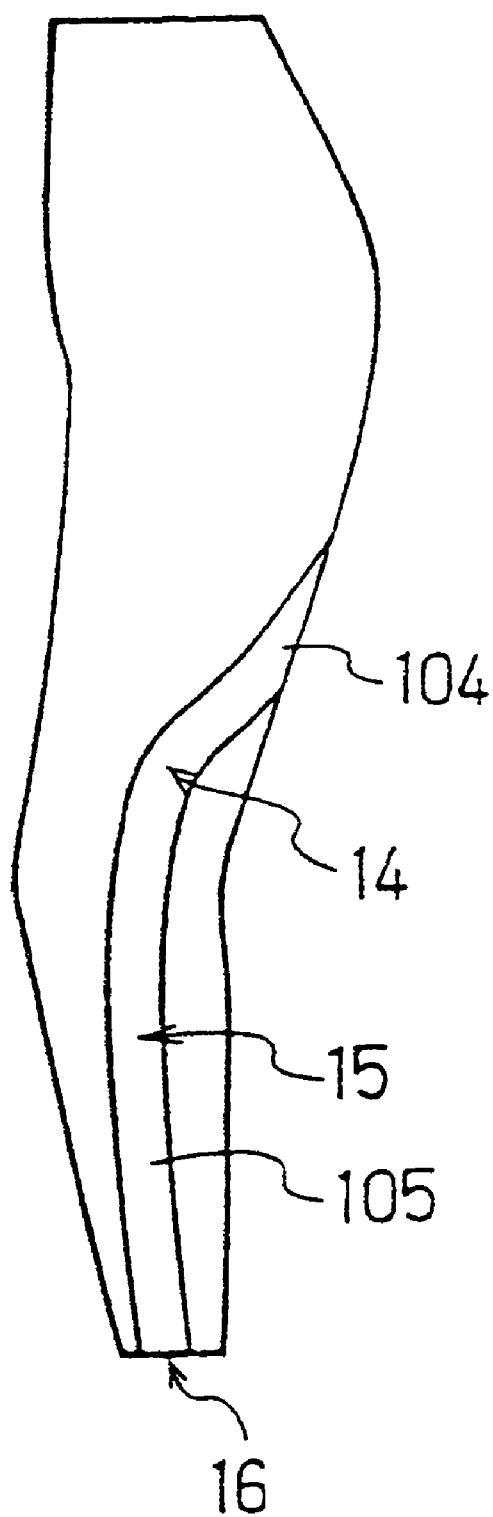
FIG. 23 is a side view of a leg protection garment of the present invention seen from the outside.

FIG. 23 is a side view showing a leg protection garment (3) of one embodiment of the present invention seen from the outside for explaining a leg protection garment in which the portion having a strong straining force 104 (B) of the leg protection garment according to FIGS. 20 and 21 further has the portion having a strong straining force 105 which ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Moreover, as shown in FIGS. 20 to 23, it is preferable for the same reason as in the above mentioned leg protection garment (1) that the portion having a strong straining force 107 (A') further has the portion having a strong straining force 103 that ranges from the vicinity 5 of the upper end of the tibia to the vicinity 7 over the attaching region of the musculus semitendinosus and the musculus semimembranosus; and that the portion having a strong straining force 104 (B) further has the portion having a strong straining force 105 which ranges from the vicinity 14 of the upper end of the fibula to the vicinity 16 of an area above the ankle by way of the vicinity 15 over the boundary between the musculus gastrocnemius and the musculus soleus so as to support the musculus gastrocnemius and the musculus soleus.

Figure 24:
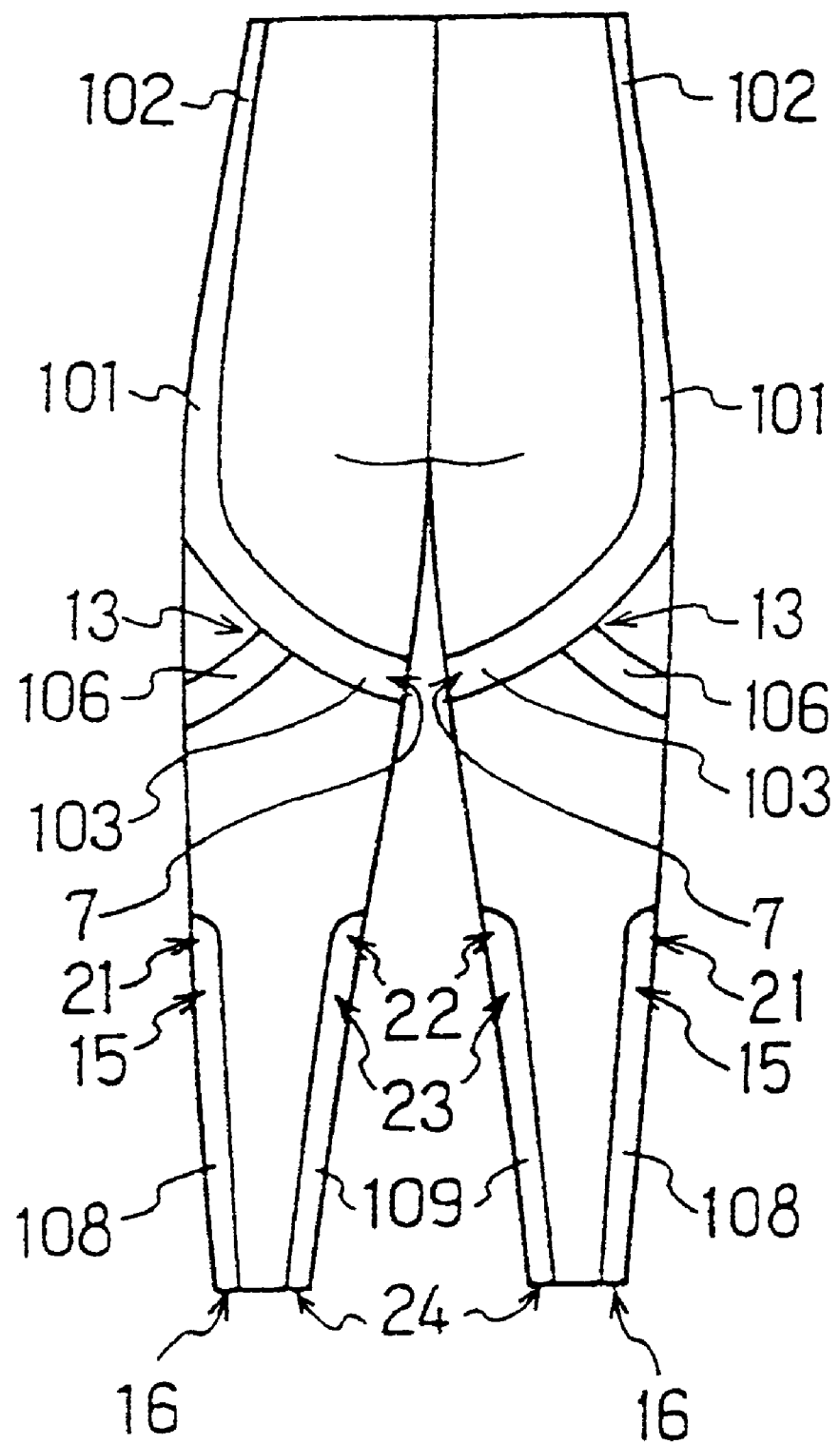
FIG. 24 is a rear view of a leg protection garment of the present invention.
Figure 25:
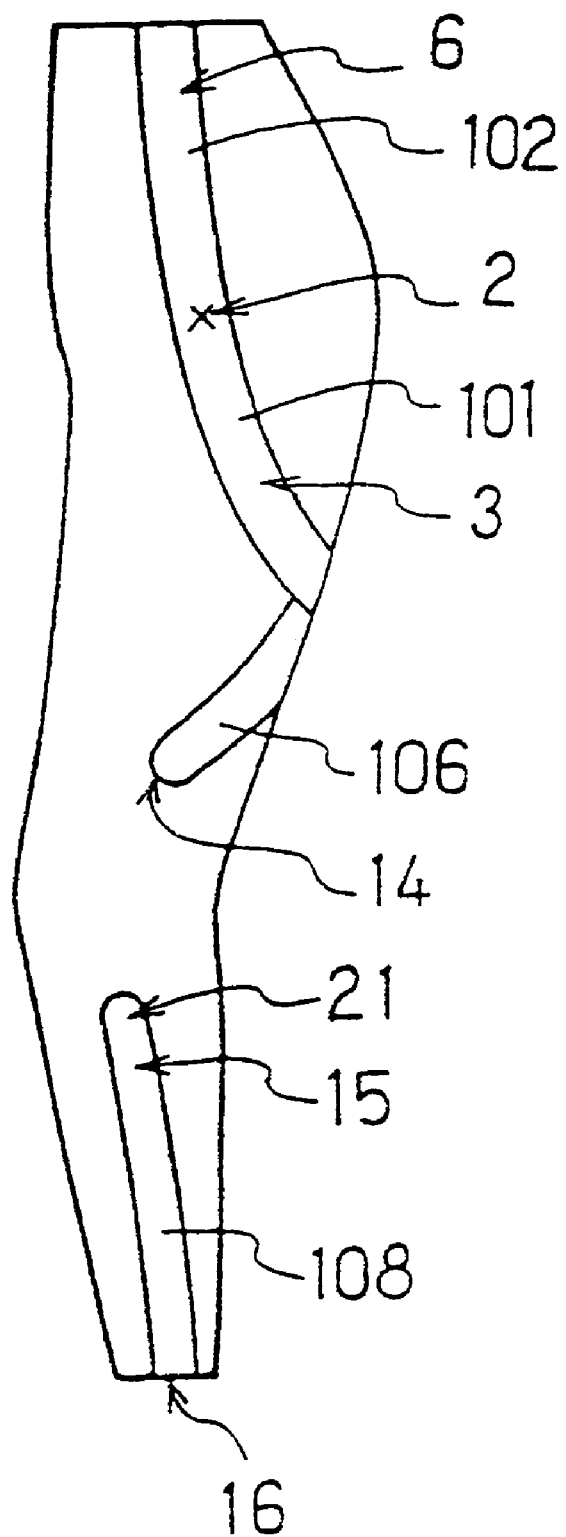
FIG. 25 is a side view of a leg protection garment of the present invention seen from the outside.

FIGS. 24 and 25 are views of a leg protection garment of one embodiment of the present invention (4) for specifically explaining that a portion having a strong straining force (C) is added as the portion having a strong straining force. This is an embodiment in which the portion having a strong straining force (A) and (B) are combined. FIG. 24 is a rear view of tights, and FIG. 25 is a side view of tights seen from the outside, respectively.

The portion having a strong straining force (C) will be explained with reference to FIG. 24. The portion having a strong straining force (C) comprises a portion having a strong straining force 108 that ranges from the upper region of the lateral crus 21 located slightly below the patella region to the vicinity 16 of an area above the ankle by way of the vicinity 15 over the boundary between the musculus gastrocnemius and the musculus soleus so as to support the musculus gastrocnemius and the musculus soleus; and a portion having a strong straining force 109 that ranges from the upper region of the medial crus 22 located slightly below the patella region to the vicinity 24 of an area above the ankle by way of the vicinity 23 over the musculus gastrocnemius and the musculus soleus so as to support the musculus gastrocnemius and the musculus soleus. The effect is to support the musculus gastrocnemius and the musculus soleus.

Figure 26:
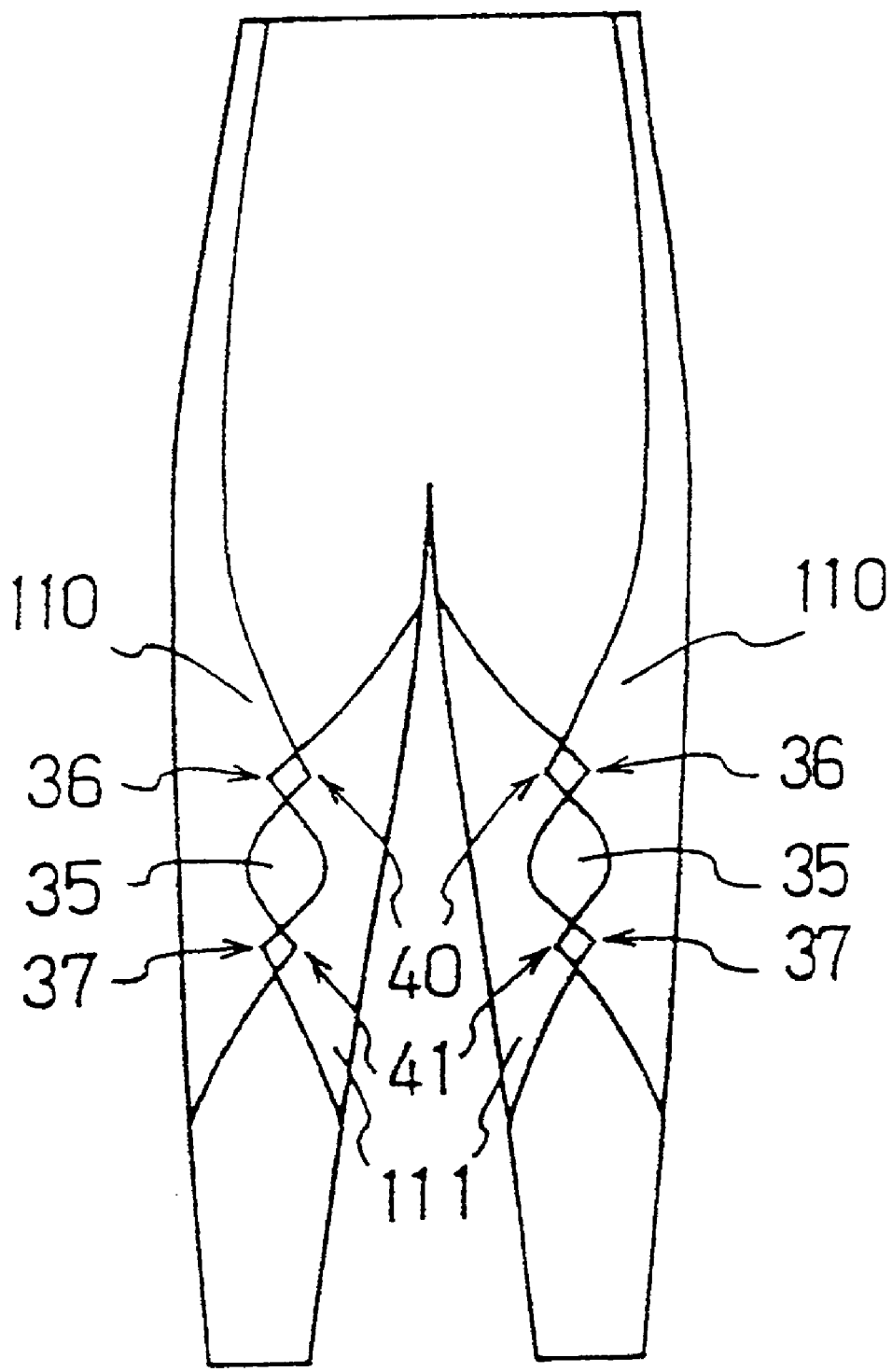
FIG. 26 is a front view of a leg protection garment of the present invention.
Figure 27:
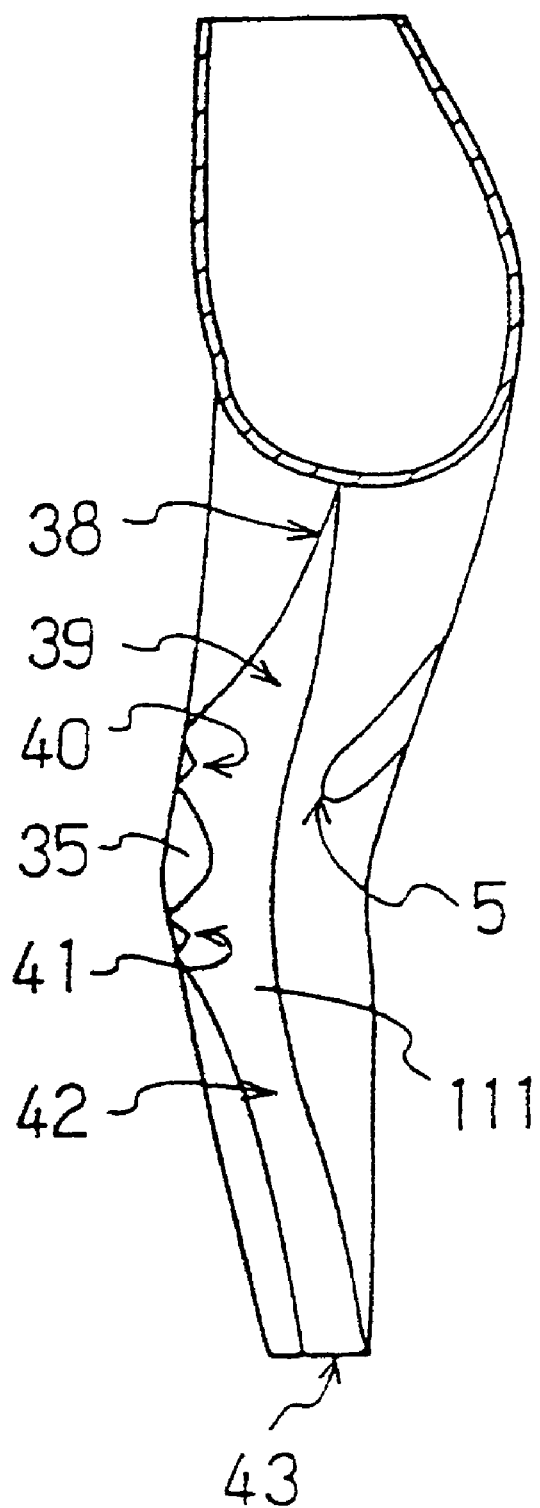
FIG. 27 is a side view of a leg protection garment of the present invention seen from the inside.
Figure 28:
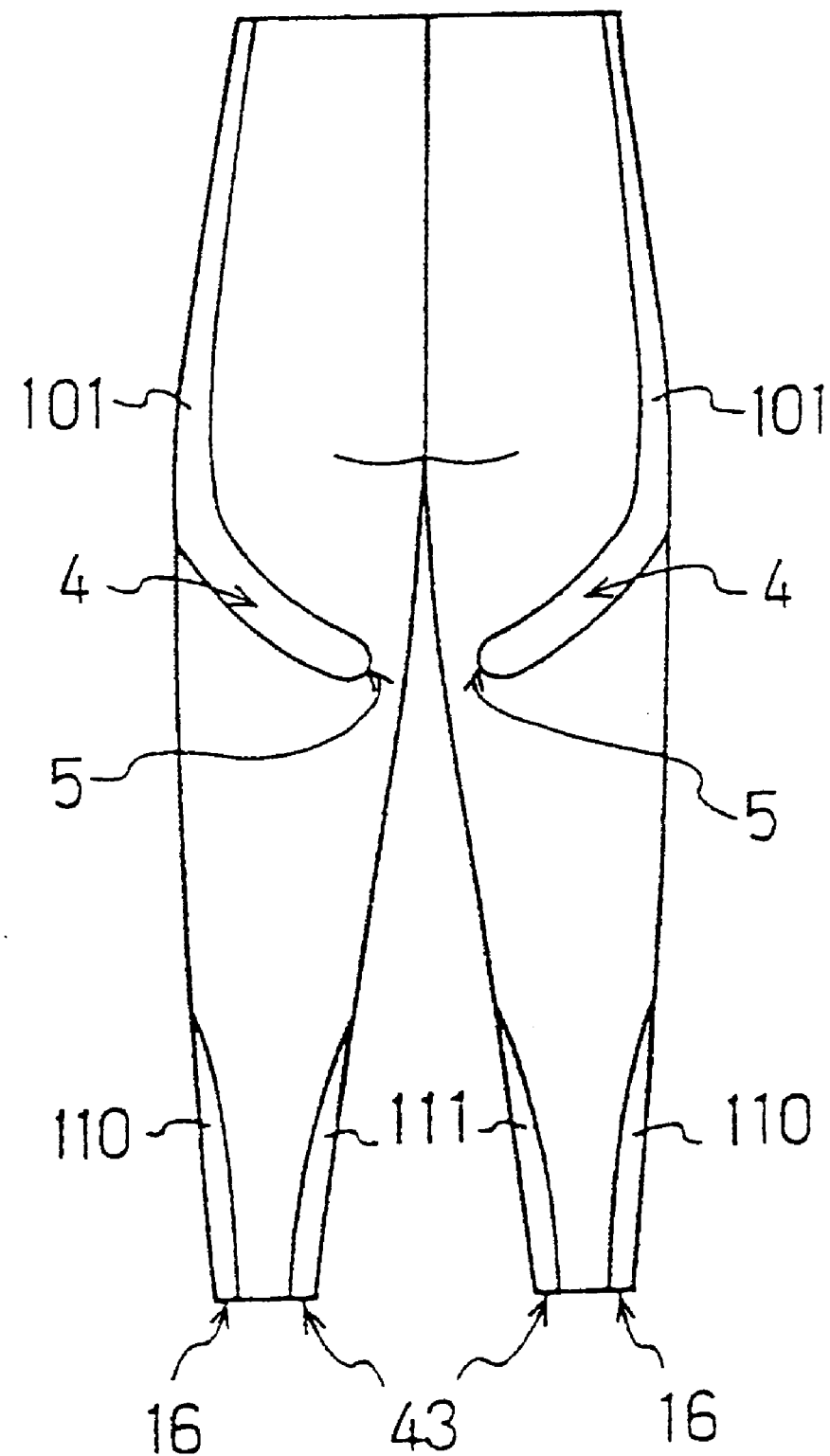
FIG. 28 is a rear view of a leg protection garment of the present invention.
Figure 29:
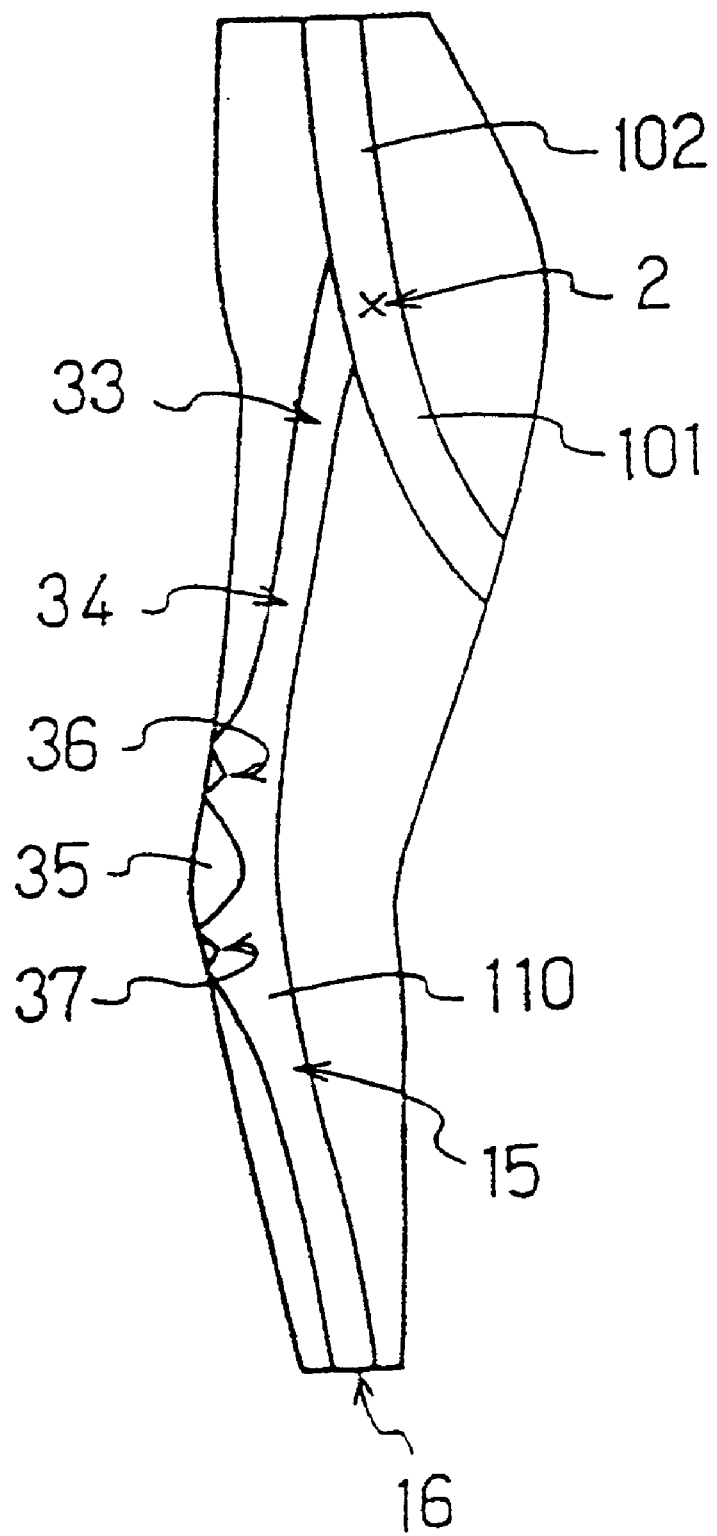
FIG. 29 is a side view of a leg protection garment of the present invention seen from the outside.

FIGS. 26 to 29 are views of a leg protection garment (5) of one embodiment of the present invention for specifically explaining that a portion having a strong straining force (()) is added as the portion having a strong straining force. This is an embodiment in which the portion having a strong straining force (D) is combined with the portion having a strong straining force (A). FIG. 26 is a front view of tights, FIG. 27 is a side view of tights seen from the inside, FIG. 28 is a rear view of tights, and FIG. 29 is a side view of tights seen from the outside, respectively.

First, the external portion 110 of a portion having a strong straining force (D) will be explained with reference to FIG. 29. The portion having a strong straining force (D) ranges from the trochanter major 2 to the side face of the patella region 35 by way of the portion 33 over the tractus iliotibialis and the portion 34 over the musculus vastus lateralis and further ranges from the side face of the patella region 35 to the vicinity 16 of an area above the ankle by way of the vicinity 15 over the boundary between the musculus gastrocnemius and the musculus soleus so as to support the musculus gastrocnemius and the musculus soleus. The effect is, to support the musculus quadriceps femoris, i.e. the muscle of the anterior side of the femoral region in an area above the patella region; and to support the musculus gastrocnemius and the musculus soleus in an area below the patella region.

Secondly, the inner side 111 of the portion having a strong straining force (D) will be explained with reference to FIG. 27. The portion having a strong straining force (D) ranges from the medial side 38 of the femur to the side face of the patella region 35 by way of the musculus vastus medialis 39 so as to support the musculus vastus medialis without crossing the muscle belly of the musculus vastus medialis, and further ranges from the side face of the patella region 35 to the vicinity 43 of an area above the ankle by way of the vicinity 42 over the boundary between the musculus gastrocnemius and the musculus soleus so as to support the musculus gastrocnemius and the musculus soleus. The effect is to support the musculus vastus medialis in an area above the patella region; and to support the musculus gastrocnemius and the musculus soleus in an area below the patella region.

Moreover, the knee region will be explained in detail with reference to FIG. 26. It is preferable in the external portion 110 that a structure is employed in which two mountain shapes 40 and 41 are formed in the medial portion above and below the patella regions 35 while avoiding the patella region 35; in the inner portion 111, the structure is employed in which two mountain shapes 36 and 37 are formed in the lateral portion above and below the patella region 35 while avoiding the patella region 35; and at the same time, each of the facing two mountain shapes 40 and 41 and two mountain shapes 36 and 37 are crossing. According to such a structure in the knee region, the garment of the present invention has the effect of supporting the ligamentum patellae or the ligamentum collateralle.

Figure 30:
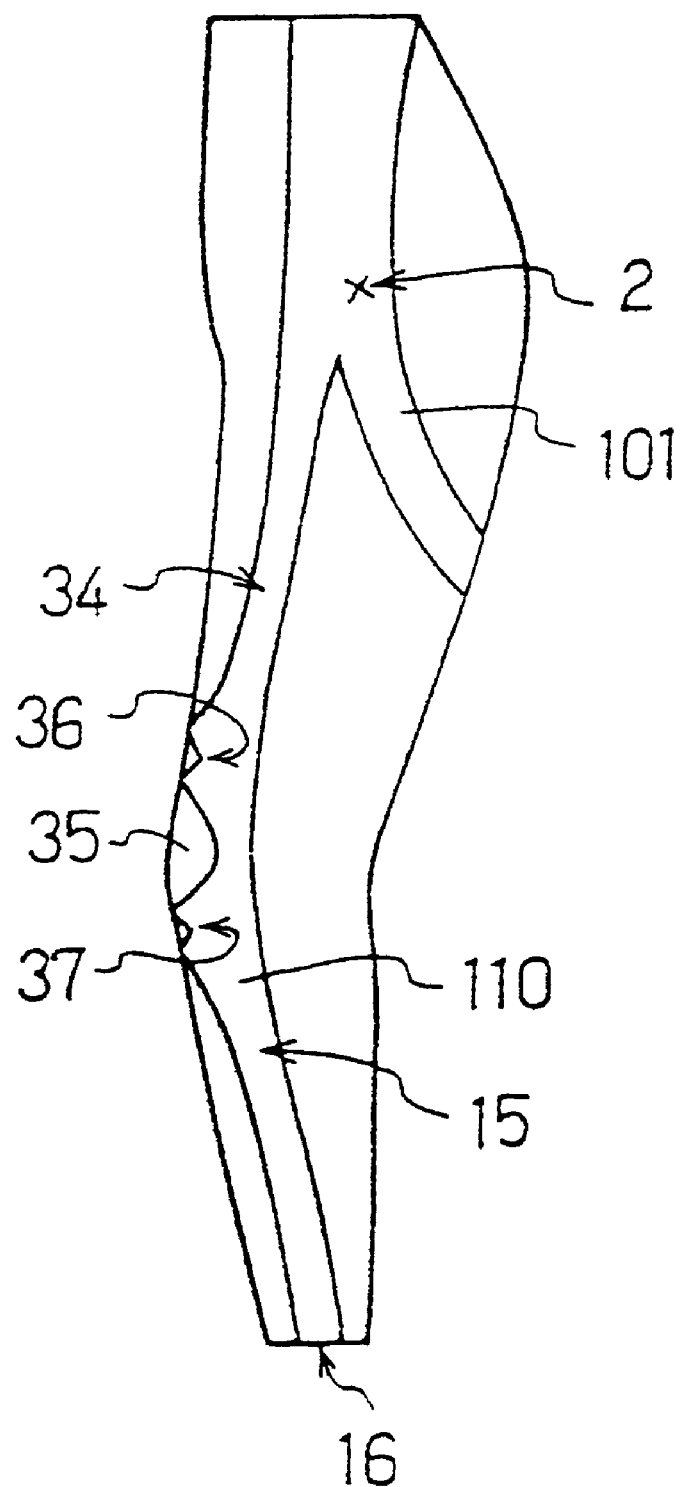
FIG. 30 is a side view of a leg protection garment of the present invention seen from the outside.

FIG. 30 is a side view showing a leg protection garment (5) of one embodiment of the present invention seen from the outside. In FIG. 30, the portions having a strong straining force (A) and (D) are made by one continuous fabric, unlike the garment of FIGS. 26 to 29 where the portions having a strong straining force (A) and (D) are made by individually separated fabrics. Also in FIG. 30, the width of the part above the trochanter major of the portion having a strong straining force (A) is wider than that shown in FIG. 29. FIG. 30 is employed as one preferable embodiment of the leg protection garment (5).

Figure 34:
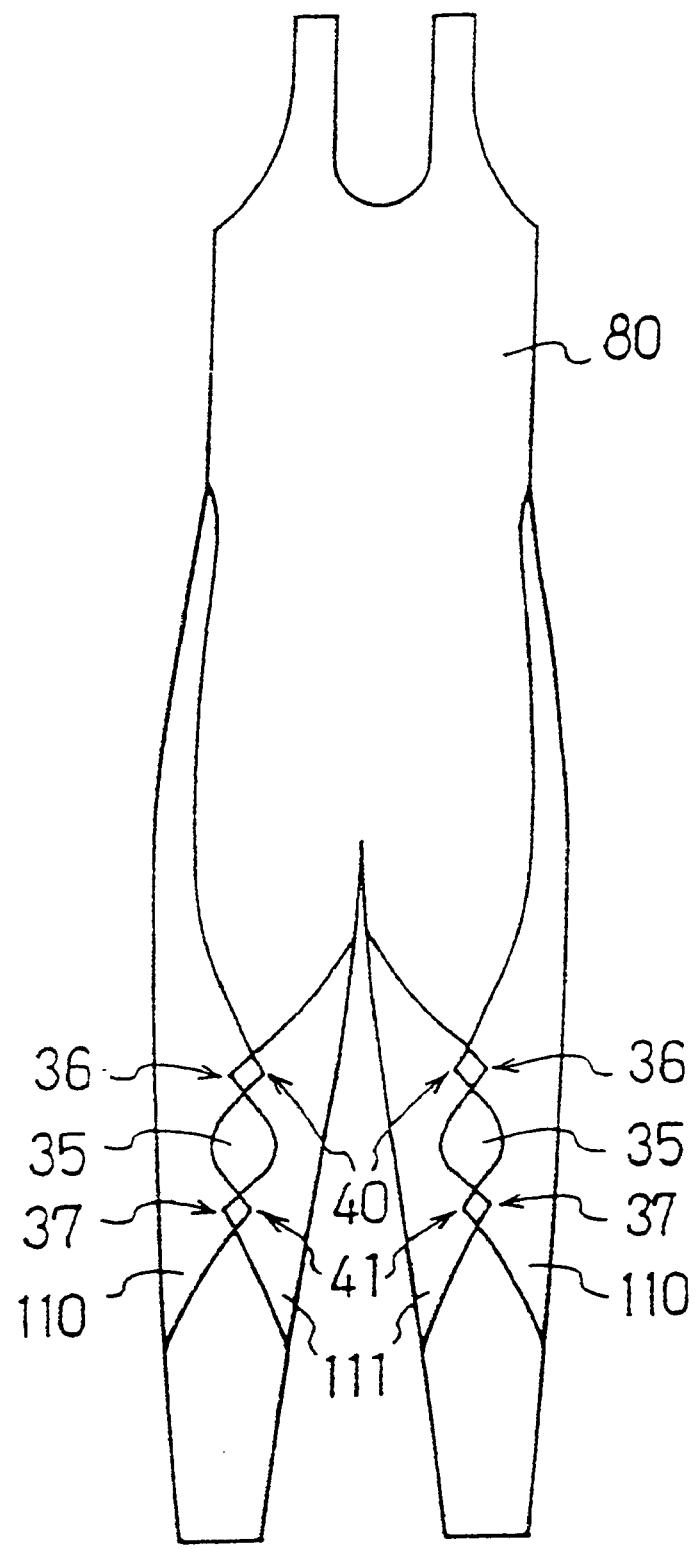
FIG. 34 is a front view of a leg protection garment of the present invention.
Figure 35:
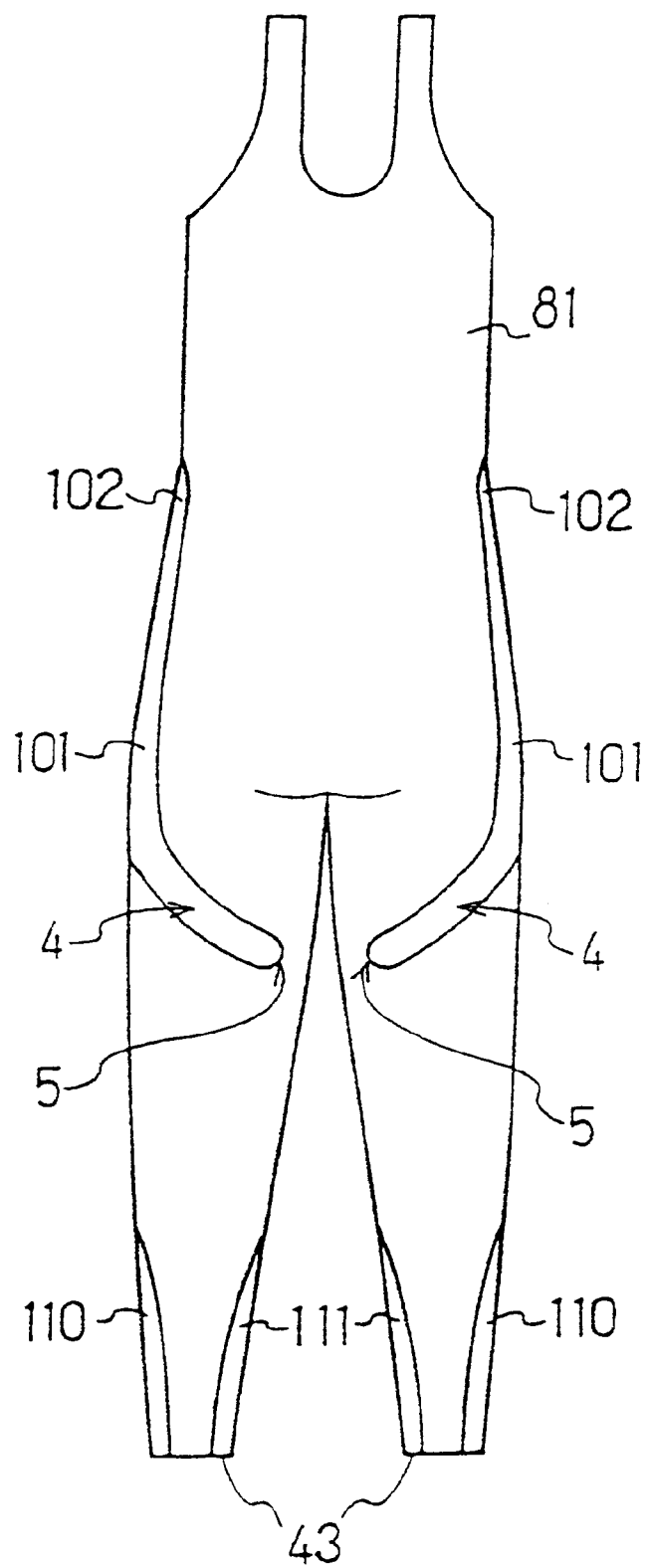
FIG. 35 is a rear view of a leg protection garment of the present invention.

FIGS. 34 and 35 are views showing a leg protection garment (5) of one embodiment of the present invention where the upper half of the body part is added to the leg protection garment according to FIG. 30. FIG. 34 is a front view of the garment, and FIG. 35 is a rear view of the garment, respectively.

The leg protection garment of the present invention is a garment having at least a lower half of the body part, however, it may have the upper half of the body part like the leg protection garments of FIGS. 34 and 35. In FIGS. 34 and 35, numerals 80 and 81 denote upper half of the body parts. However, the leg protection garment having a upper half of the body part is not limited to the above mentioned embodiments alone and may be applied to every other embodiment.

Figure 31:
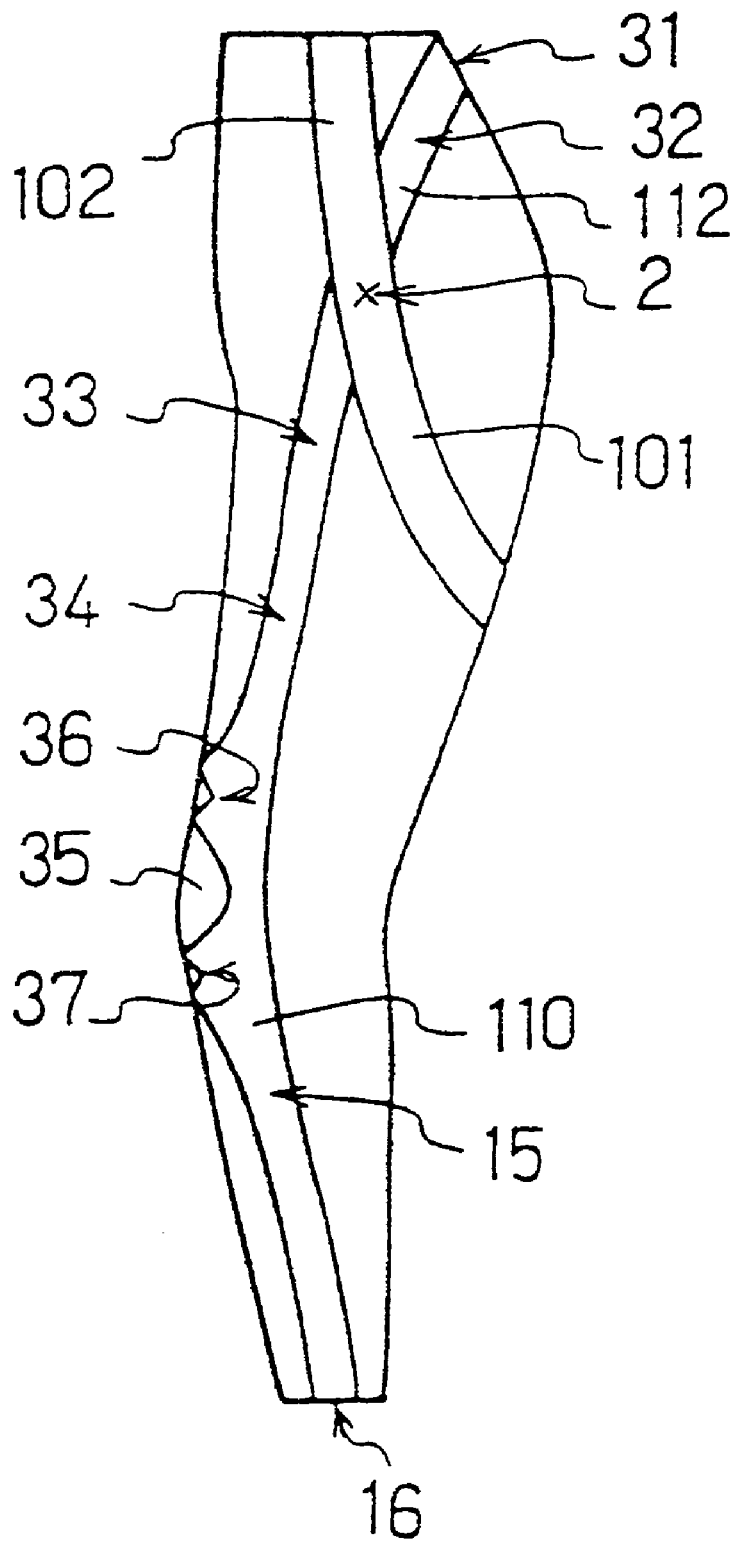
FIG. 31 is a side view of a leg protection garment of the present invention seen from the outside.

FIG. 31 is a side view showing a leg protection garment (6) of one embodiment of the present invention seen from the outside for specifically explaining that a portion having a strong straining force (D) is added as the portion having a strong straining force.

As shown in FIG. 31, the portion having a strong straining force (D'), in an area above the trochanter major 2 of the portion having a strong straining force (D), has an extended portion having a strong straining force 112 which ranges from the outside 31 of the hip to the trochanter major 2 by way of the portion 32 over the musculus glutaeus maximums. The extended portion having a strong straining force 112 above the trochanter major 2 has an effect of supporting the musculus glutaeus maximus.

Figure 32:
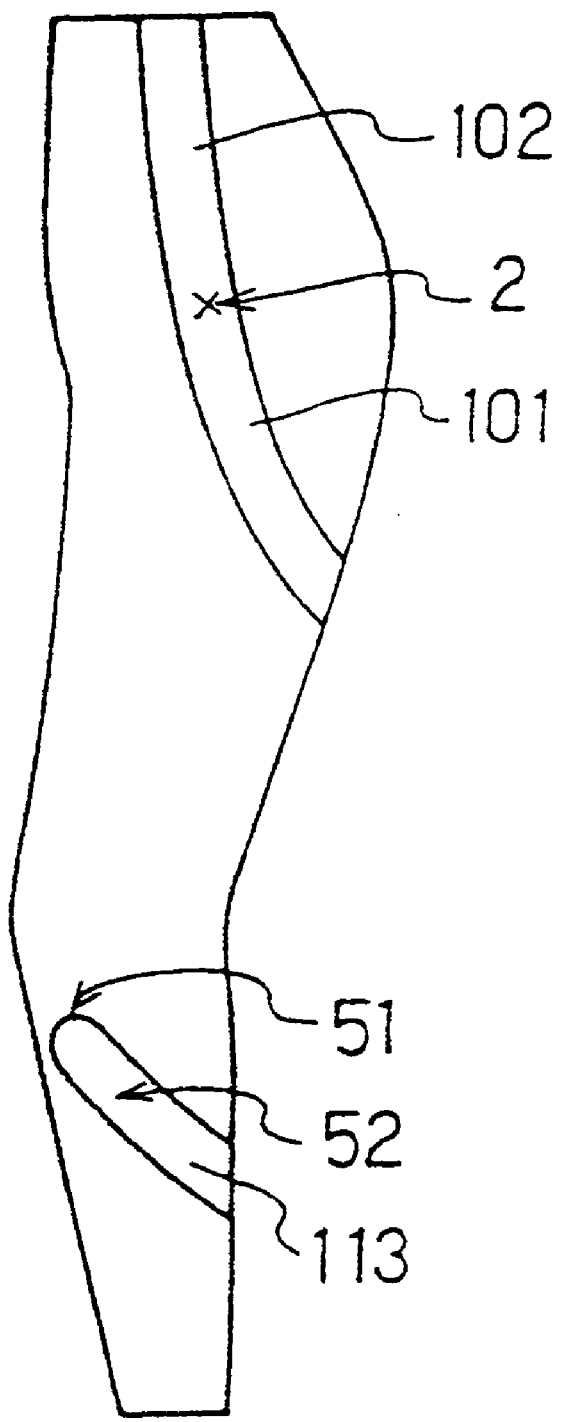
FIG. 32 is a side view of a leg protection garment of the present invention seen from the outside.
Figure 33:
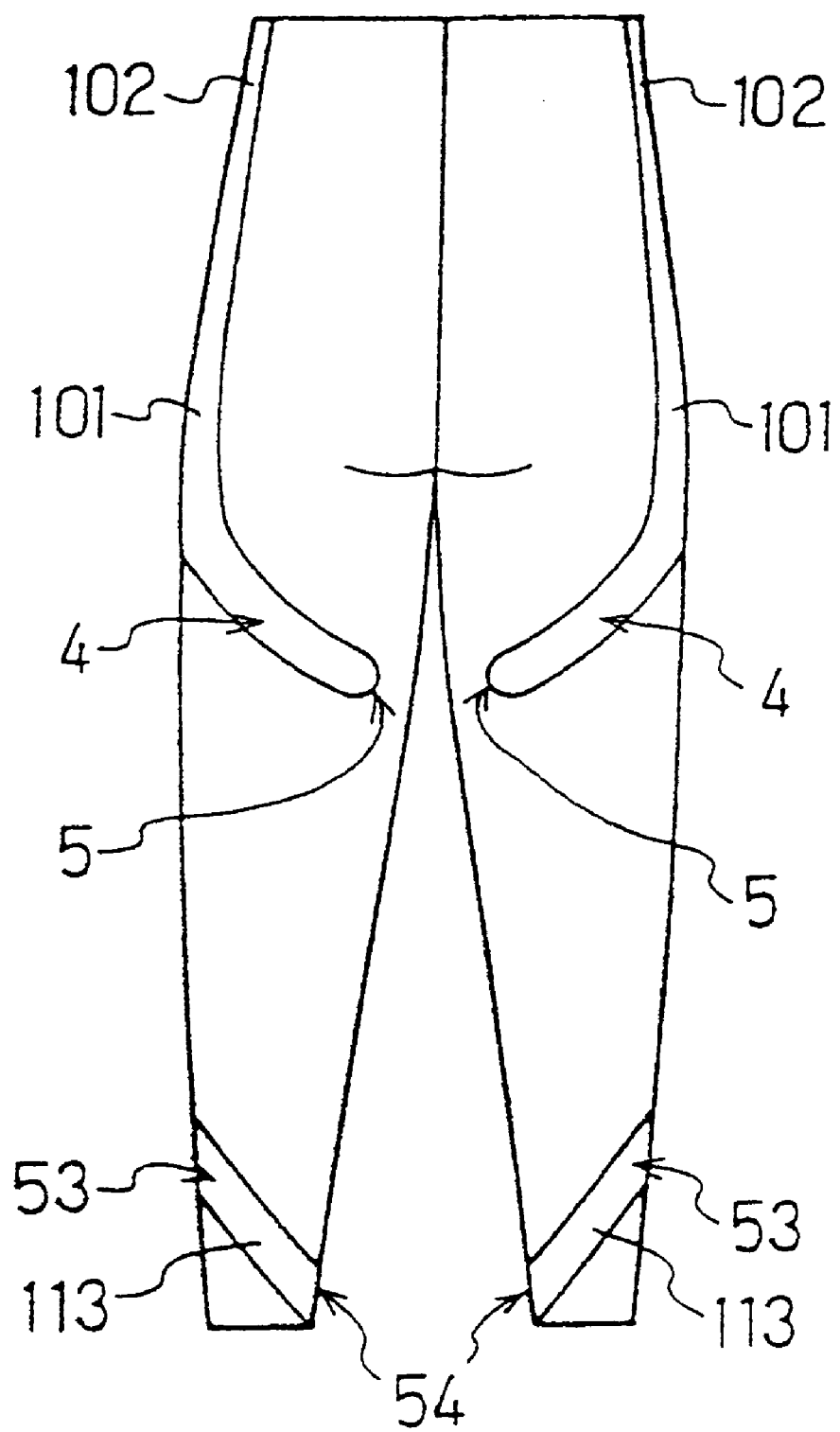
FIG. 33 is a rear view of a leg protection garment of the present invention.

FIGS. 32 and 33 are views showing a leg protection garment (7) of one embodiment of the present invention for specifically explaining that the portion having a strong straining force 113 (E) is added as the portion having a strong straining force. They are employed as embodiments in which the portion having a strong straining force (E) is combined with the portion having a strong straining force (A). FIG. 32 is a side view of tights seen from the outside, and FIG. 33 is a rear view of tights, respectively.

The portion having a strong straining force 113 (E) will be explained with reference to FIGS. 32 and 33. The portion having a strong straining force 113 ranges from the upper region 51 of the lateral crus located slightly below the patella region to the vicinity 54 of an area above the ankle by way of the vicinity 52 over the boundary between the musculus gastrocnemius and the musculus soleus so as to support the musculus gastrocnemius and the musculus soleus, wherein the portion obliquely crosses the tendon region 53 located below the muscle belly of the musculus gastrocnemius without crossing the muscle belly of the musculus gastrocnemius. The effect is to support the musculus gastrocnemius and the musculus soleus.

As mentioned above, the specific embodiments of the present invention are explained with reference to FIGS. 1 to 35. As mentioned above, the leg protection garment of the present invention is not limited to the embodiments shown in the figures. For example, in FIGS. 1 to 35, the vicinity 5 of the upper end of the tibia and the vicinity 7 over the attaching region of the musculus semitendinosus and the musculus semimembranosus are shown to be located in the relatively upper location in the portion having a strong straining force (A); and an area 11 above the musculus semimembranosus and the vicinity 12 over the boundary between the musculus semimembranosus and the musculus adductor magnus are shown to be located in the relatively upper location in the portion having a strong straining force (B). For references, views in which the above mentioned locations are located in a lower portion of the tights are shown in FIGS. 36 to 38 as examples.

Figure 36:
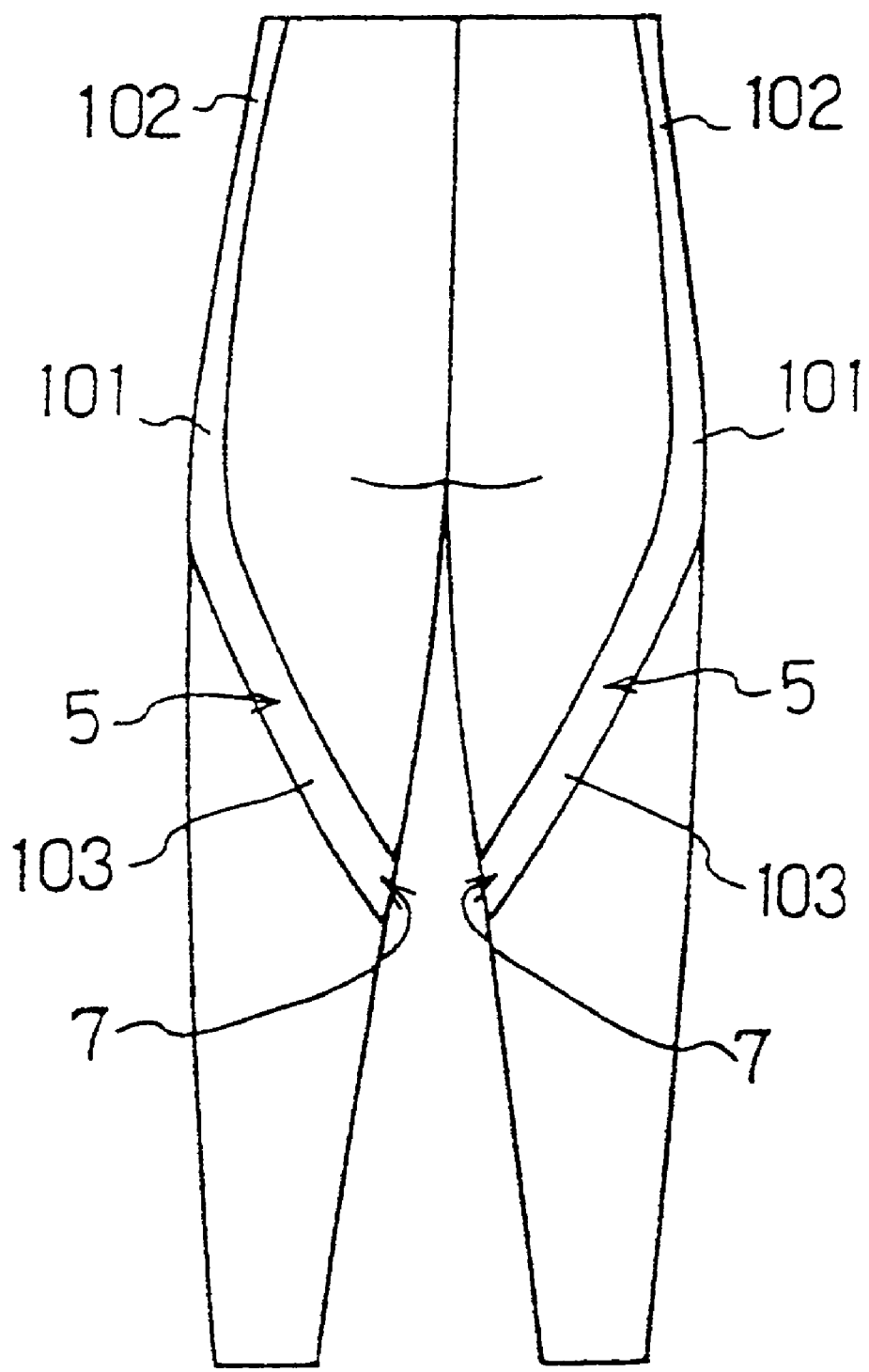
FIG. 36 is a rear view of a leg protection garment of the present invention.

FIG. 36 is an example in which the vicinity 5 of the upper end of the tibia and the vicinity 7 over the attaching region of the musculus semitendinosus and the musculus semimembranosus in the portion having a strong straining force (A) are located at a relatively lower location. FIG. 36 is a rear view of the leg protection garment in which the portion having a strong straining force 101 (A) has the portion having a strong straining force 102 which passes over the portion 6 over the musculus tensor fasciae latae in the upper portion of the trochanter major, and the portion having a strong straining force 103 which ranges from the vicinity 5 of the upper end of the tibia to the vicinity 7 of the attaching region of the musculus semitendinosus and the musculus semimembranosus.

Figure 37:
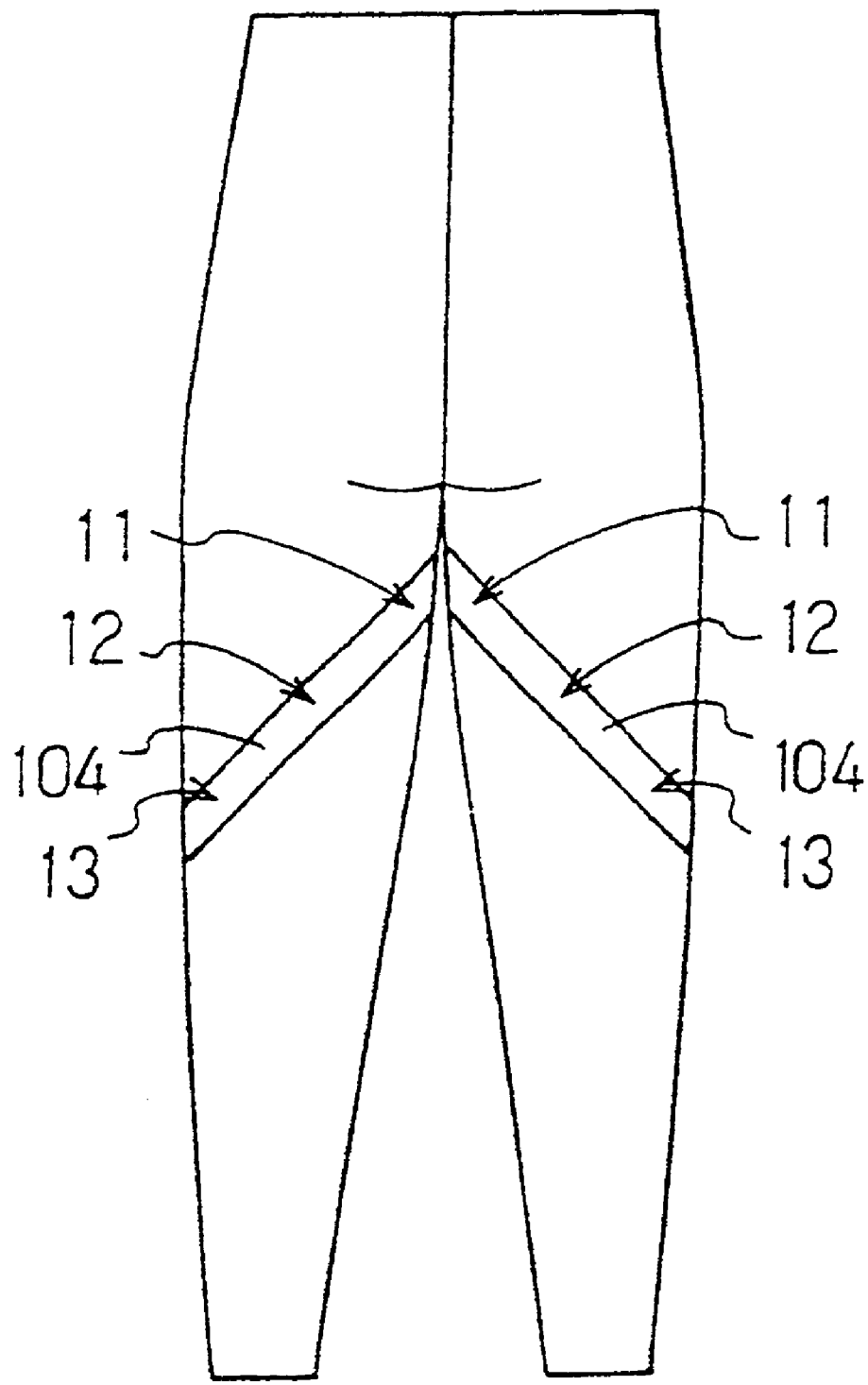
FIG. 37 is a rear view of a leg protection garment of the present invention.

FIG. 37 is an example of a leg protection garment in which an area 11 above the musculus semimembranosus and the vicinity 12 over the boundary between the musculus semimembranosus and the musculus adductor magnus in the portion having a strong straining force (B) are located at relatively lower location. FIG. 37 is a rear view of a leg protection garment having only the portion having a strong straining force 104 (B).

Figure 38:
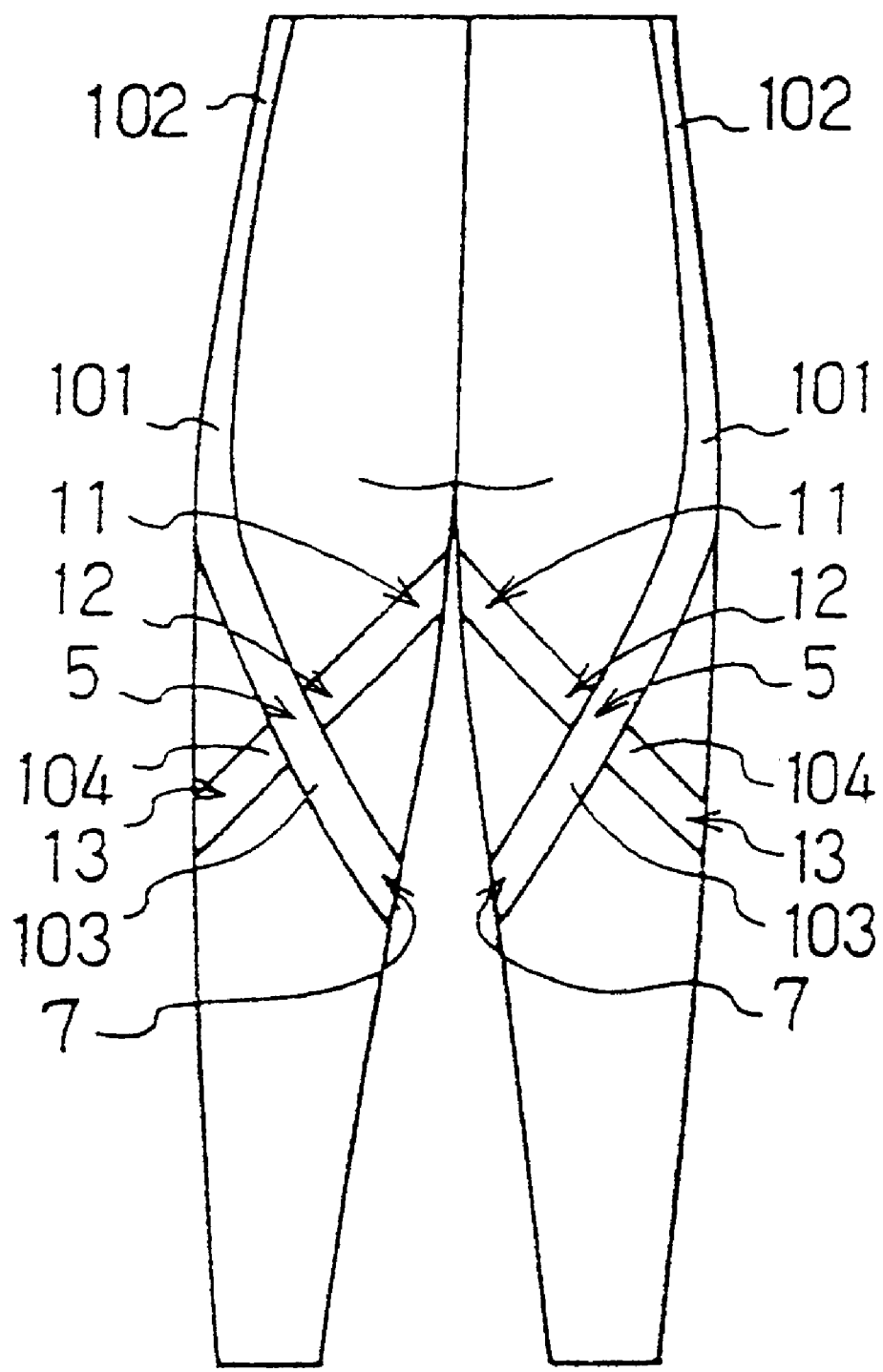
FIG. 38 is a rear view of a leg protection garment of the present invention.

FIG. 38 is rear view of a leg protection garment combining the portion having a strong straining force (A) according to FIG. 36 and the portion having a strong straining force (B) according to FIG. 37.

The leg protection garment of the present invention is formed of stretchable fabric and has a portion whose straining force is partially strong (a portion having a strong straining force).

As the method for providing the portion having a strong straining force in the leg protection garment of the present invention, the portion having a strong straining force may be formed in a way in which a predetermined shaped stretchable fabric is overlapped with the garment's main part by stitching, and may be formed in a way in which a predetermined shaped stretchable fabric is overlapped with the garment's main part by adhering. According to these methods, a garment having a durability can easily be manufactured. Needless to say, each part of a portion having a strong straining force and other parts may be made as the predetermined shapes of individual parts and sewn into one to thus form the leg protection garment of the present invention, however, such a method requires complicated sewing and takes somewhat much labor and time.

In addition, for example, the portion having a strong straining force may be formed in a way in which the predetermined shaped stretchable fabric is stretched and overlapped with the garment's main part by stitching or adhering. These methods are preferred in the case of providing a stronger straining force with the portion having a strong straining force.

Moreover, the portion having a strong straining force may be formed in a way in which elastic resin is impregnated, or elastic resin film is adhered, to the predetermined portion of the garment's main part. By such methods, the portion having a strong straining force of a relatively thin thickness can be obtained. As the elastic resin, polyurethane resin, polyester elastomer resin, or other appropriate elastic resin can be applied.

Moreover, the portion having a strong straining force may be formed by using an elastic fiber having a thicker thickness than that of any other location in fiber materials constituting the garment's main part. By such a method, since overlapping is not required, the portion having a strong straining force having thinner thickness can be obtained.

Moreover, the portion having a strong straining force may be formed by making a texture of a knitted fabric having a stronger straining force than a texture of knitted fabric of the stretchable fabric constituting the garment's main part. Also by such a method, since overlapping is not required, the portion having a strong straining force having thinner thickness can be obtained.

Among the above mentioned methods for providing the portion having a strong straining force, the method of overlapping the predetermined shaped stretchable fabric with the garment's main part by stitching and the method in which the predetermined shaped stretchable fabric is stretched and overlapped with the garment's main part by stitching are preferred. Moreover, according to these methods, the straining force of the stretchable fabric stitched to the garment's main part may be somewhat smaller than, or the same as, or larger than the straining force of the stretchable fabric of the garment's main part. As a result of a stretchable fabric being overlapped onto the garment's main part, the straining force of the overlapped portion is increased. The level of the straining force of the fabric to be overlapped is appropriately determined in accordance with kinds of sports, the level of disorders of each user or the disorders to be prevented or the level of the straining force of the garment's main parts.

The straining force in the portion having a strong straining force is not limited, but it is preferable that the straining force is designed to be approximately 30 to 400 gf in the longitudinal direction. It is preferred that in the range of straining forces that the effect of the present invention can efficiently be exhibited, such that the compression is not too strong and the fit is comfortable.

As a method of measuring a straining force, an Instron type All Round Specimen-Extension tensile tester ("AUTOGRAPH" AG-500D made by Shimadzu Corporation) is used to conduct three cycles of stretch and recovery testing at a rate of stressing of 300±20 mm/min to 80% of the sample length (free length of test piece between grips). On the third stretch and recovery cycle, the value in a 30% stretched state and the value at the recovery are measured, and only the value at the recovery is recorded and defined as the straining force. Preferably, the size of the sample should be 2.5 cm in width and 16 cm in length, wherein 2.5 cm of the length is gripped by the upper test piece, 3.5 cm of the length is gripped by the lower test piece, and 10 cm is the remaining length used for the tensile test. If such a preferred size of the sample cannot be cut out from the garment to be measured, samples having a smaller size than the above may be used. However, the smaller the size of the sample, the greater the measurement error. Therefore, it is preferable that the largest cuttable samples be taken and measured. Moreover, in a case where the portion having the straining force is formed by overlapping a stretchable fabric onto the garment's main part, the measurement on the portion of that sample having the straining force is, needless to say, carried out on samples of the overlapped portion.

The width of the portion having a strong straining force of the leg protection garment of the present invention is not particularly limited and is appropriately determined within a scope suitable to achieve the object of the present invention in accordance with the location of the portion having a strong straining force, the strength of the straining force of the material to be used, the means of forming the portion having a strong straining force and the level or locations of the disorders of each user, or the purpose of preventing the disorders, whether the user is a child or an adult, or the like. For example, the portion having the widest width is usually about 5 to 15 cm, more preferably about 8 to 13 cm. The width of the other portions having a strong straining force is: the width of the portion having the narrowest width, for example, outside of the lateral side of the femoral region is usually about 2 to 10 cm, more preferably about 4 to 8 cm. Needless to say, as long as the objects of the present invention can be attained, the width of the portion having a strong straining force may be partially wider or narrower as necessary.

As the stretchable fabrics used for the garment's main part or each portion having a strong straining force of the leg protection garment of the present invention, power net containing polyurethane fiber that is stretchable rochelle knitted fabric containing polyurethane fiber, two directions stretchable tricot knitted fabric containing polyurethane fiber that is tricot knitted fabric containing polyurethane fiber, or the like can preferably be used. Consequently, as compared with the conventional supporters etc. using the relatively thick pile fabric or neoprene sheet etc., the fabric-having a thickness required for the general garment, for example, having a thickness of about 0.3 to 0.8 mm can be used, and therefore the leg protection garment having little deterioration of appearance, for example, a proportion in use, being well fitted to the body, and having excellent ventilation can be provided. The types of power net include, for example, plain power net, satin-like power net, two directions stretchable rochelle, "Toriskin™" (the product of Urabe Corporation) etc. Moreover, incidentally, in the tights according to FIGS. 1 to 38, as the fabric constituting the tights' main part, two directions stretchable tricot knitted fabric composed of a stretchable material, consisting of 80% polyester fiber and 20% polyurethane fiber (the straining force: 45 gf in the approximately horizontal direction of tights; and 33 gf in the approximately longitudinal direction of tights) was used; as the fabric lining the portion having a straining force, power net knitted fabric composed of a stretchable material consisting of 62% nylon fiber and 38% polyurethane fiber (the straining force: 272 gf in the longitudinal direction of the lining materials; and 88 gf in the wide direction of the lining material) was used. However, needless to say, the chosen fabric is not limited to these alone.

All of the portions having a strong straining force are not necessarily the same. A different straining force may be applied in accordance with the portions.

Industrially Applicability (1) The leg protection garment of the present invention has a lower half of the body part which has a leg portion of length capable of covering at least the patella region and is formed of stretchable fabric, in which the garment has a portion having a partially strong straining force and comprises the portion expressed by at least the following (A) and/or (B) as the portion having a strong straining force. By such an embodiment, the present invention provides a leg protection garment in which the portion having a strong straining force supports the musculus biceps femoris from the side; helps the musculus biceps femoris to contract; and in turn supports the flexion of the articulatio genus, the extension of the articulatio coxae, and the excycloduction of the articulatio genus during the semiflexion of the knee; and the portion having a strong straining force supports the musculus semitendinosus and the musculus semimembranosus from the side; helps the musculus semitendinosus and musculus semimembranosus to contract; and in turn supports the flexion of the articulatio genus, the extension of the articulatio coxae, and the intorsion of the lower leg during the semiflexion of the knee by supporting the musculus semitendinosus. Moreover, by supporting the musculus biceps femoris, the musculus semitendinosus and the musculus semimembranosus, in various kinds of sports requiring the flexion of the articulatio genus, disorders in the ligament of the knee or in the meniscus can be relieved. In addition, by supporting the musculus biceps femoris, the musculus semitendinosus and the musculus semimembranosus, the massage effect is generated and the flow of blood and lymphocyte is promoted, thus improving the recovery of the muscle from fatigue due to the exhaustion of energy or the accumulation of lactic acid.

(A) a portion having a strong straining force which ranges from an area above the trochanter major 1 to the vicinity 5 of the upper end of the tibia by way of the trochanter major 2 and further the vicinity over the musculus biceps femoris and/or the tractus iliotibialis 80 as to support the musculus biceps femoris, wherein the portion passes the vicinity 4 of the tendon region located below the muscle belly of the musculus biceps femoris without crossing the muscle belly of the musculus biceps femoris at a right angle with respect to the direction of the muscle fiber;

(B) a portion having a strong straining force which ranges from an area 11 above the musculus semimembranosus to the vicinity 14 of the upper end of the fibula by way of the vicinity over the musculus semimembranosus and/or the musculus adductor magnus so as to support the musculus semitendinosus and the musculus semimembranosus, wherein the portion passes the vicinity 13 of the tendon region located below the muscle belly of both the musculus semitendinosus and the musculus semimembranosus without crossing the muscle belly of the musculus semitendinosus and the musculus semimembranosus at a right angle with respect to the direction of the muscle fiber.

Moreover, in addition to the above mentioned effects, the garment of the present invention: can easily and adequately be put on and taken off if necessary, for example, when taking a bath etc., by ordinary people; it therefore, does not require a treatment by the skilled person as in the case of the taping treatment and can readily be put on; and furthermore is effective for promoting the prevention or treatment of disorders etc. in the leg muscle etc.

In addition, since the portion having a strong straining force is incorporated into the garment, the tightness and looseness of the compression can be obtained while in motion without causing discomfort, that is, the portion where the taping is applied is always subjected to the compression as in the case of the taping treatment. Consequently, the leg protection garment of the present invention provides a comfortable fit to a user due to a lower supporting force when he or she is not in motion, on the other hand, it can exhibit an appropriate straining force while a user is in motion. Therefore, it provides a good comfortable feeling in use and is effective for promoting the prevention or treatment of disorders etc. in the leg muscle.

Moreover, since a tape is not closely contacted to the skin of the human body with an adhesive agent, as in the case of a taping treatment, the hygienic problems, for example, the occurrence of itchy skin resulting from stuffiness, can be improved.

In addition, the present invention can provide a leg protection garment that does not deteriorate in appearance, e.g. a proportion in use, and which has relatively excellent ventilation.

In the above mentioned leg protection garment of the present invention (1), by the following embodiments (I), (II), and (III), the leg protection garment capable of supporting the musculus gastrocnemius and the musculus soleus can be provided as well:

(I) an embodiment in which the portion (A) further has a portion having a strong straining force which, in an area above the trochanter majors, passes over at least one muscle selected from the group consisting of the musculus tensor fasciae latae, the tractus iliotibialis, and the musculus glutaeus medius (preferably in the portion 6 over the musculus tensor fasciae latae);

(II) an embodiment in which the portion (A) further has a portion having a strong straining force which ranges from the vicinity 5 of the upper end of the tibia to the vicinity 7 of the attaching region of the musculus semitendinosus and the musculus semimembranosus; and (III) an embodiment in which the portion (B) further has a portion having a strong straining force which ranges from the vicinity 14 of the upper end of the fibula to the vicinity 16 of an area above the ankle by way of the vicinity over the musculus gastrocnemius and/or the musculus soleus so as to support the musculus gastrocnemius and the musculus soleus (preferably in the vicinity 15 over the boundary between the musculus gastrocnemius and the musculus soleus).

(2) Moreover, the leg protection garment of the present invention has a lower part which has a leg portion of length capable of covering at least the patella region and formed of stretchable fabric, in which the garment has a portion having a partially strong straining force and comprises the portion expressed by at least the following (A) and (B) as the portion having a strong straining force. By such an embodiment, the present invention can provide a leg protection garment capable of supporting the musculus semitendinosus and the musculus semimembranosus in addition to the main support, namely, the support of the musculus biceps femoris.

(A) a portion having a strong straining force which ranges from an area above the trochanter major 1 to the vicinity 5 of the upper end of the tibia by way of the trochanter major 2 and further the vicinity over the musculus biceps femoris and/or the tractus iliotibialis so as to support the musculus biceps femoris from the side, wherein the portion passes the vicinity 4 of the tendon region located below the muscle belly of the musculus biceps femoris without crossing the muscle belly of the musculus biceps femoris at right angle with respect to the direction of the muscle fiber; and (B') a portion having a strong straining force which ranges from the vicinity 13 of the tendon region located below the muscle belly of both the musculus semitendinosus and the musculus semimembranosus to the vicinity 14 of the upper end of the fibula.

Moreover, in the above mentioned leg protection garment of the present invention, by the following (I), (II), and (III), the leg protection garment having the same effect as the above (1) can be provided:

(I) an embodiment in which the portion (A) further has a portion having a strong straining force which, in an area above the trochanter major, passes over at least one muscle selected from the group consisting of the musculus tensor fasciae latae, the tractus iliotibialis, and the musculus glutaeus medius (preferably in the portion 6 over the musculus tensor fasciae latae);

(II) an embodiment in which the portion (A) further has a portion having a strong straining force which ranges from the vicinity 5 of the upper end of the tibia to the vicinity 7 of the attaching region of the musculus semitendinosus and the musculus semimembranosus; and (III) an embodiment in which the portion (B') further has a portion having a strong straining force which ranges from the vicinity 14 of the upper end of the fibula to the vicinity 16 of an area above the ankle by way of the vicinity of the musculus gastrocnemius and/or the musculus soleus (preferably in the portion 15 over the boundary between the musculus gastrocnemius and the musculus soleus) so as to support the musculus gastrocnemius and the musculus soleus.

(3) Moreover, the leg protection garment of the present invention has a lower half of the body part that has a leg portion of length capable of covering at least the patella region and is formed of stretchable fabric, wherein the garment has a portion having a partially strong straining force and comprises the portion expressed by at least the following (A') and (B) as the portion having a strong straining force. By such an embodiment, the present invention can provide a garment comprising the support of the musculus biceps femoris in addition to the main support, namely, the support of the musculus semitendinosus and musculus semimembranosus.

(A') the portion having a strong straining force which ranges from the vicinity 4 of the tendon region located below the muscle belly of the musculus biceps femoris to the vicinity 5 of the upper end of the tibia; and (B) the portion having a strong straining force which ranges from an area 11 above the musculus semimembranosus to the vicinity 14 of the upper end of the fibula by way of the vicinity over the musculus semimembranosus and/or the musculus adductor magnus so as to support the musculus semitendinosus and the musculus semimembranosus, wherein the portion passes the vicinity 13 of the tendon region located below the muscle belly of both the musculus semitendinosus and the musculus semimembranosus without crossing the muscle belly of the musculus semitendinosus and the musculus semimembranosus at right angle with respect to the direction of the muscle fiber.

Moreover, in the above mentioned leg protection garment, by the following embodiments (I), and (II), the leg protection garment having the same effect as the above mentioned (1) can be provided.

(I) an embodiment in which the portion (A') further has a portion having a strong straining force which ranges from the vicinity 5 of the upper end of the tibia to the vicinity 7 over the attaching region of the musculus semitendinosus and the musculus semimembranosus;

(II) an embodiment in which the portion (B) further has a portion having a strong straining force which ranges from the vicinity 14 of the upper end of the fibula to the vicinity 16 of an area above the ankle by way of the vicinity over the musculus gastrocnemius and/or the musculus soleus (preferably in the vicinity 15 over the boundary between the musculus gastrocnemius and the musculus soleus) so as to support the musculus gastrocnemius and the musculus soleus.

(4) Moreover, in the leg protection garment of the present invention, by such a preferred embodiment where a portion having a strong straining force (C) comprises a portion having a strong straining force which ranges from the upper region of the lateral crus 21 located slightly below the patella region to the vicinity 16 of an area above the ankle by way of the vicinity over the musculus gastrocnemius and/or the musculus soleus (preferably in the vicinity 15 over the boundary between the musculus gastrocnemius and the musculus soleus) so as to support the musculus gastrocnemius and the musculus soleus; and a portion having a strong straining force which ranges from the upper region of the medial crus 22 located slightly below the patella region to the vicinity 24 of an area above the ankle by way of the vicinity of the musculus gastrocnemius and/or the musculus soleus (preferably in the vicinity 23 over the boundary between the musculus gastrocnemius and the musculus soleus) so as to support the musculus gastrocnemius and the musculus soleus, the leg protection garment capable of supporting the musculus gastrocnemius and the musculus soleus can be provided.

(5) Moreover, in the leg protection garment of the present invention, by such a preferred embodiment where a portion having a strong straining force (D) comprises a lateral portion which ranges from the vicinity of the trochanter major to the patella region 35 by way of the vicinity over the tractus iliotibialis and/or musculus vastus lateralis, and further ranges from the patella region 35 to the vicinity 16 of an area above the ankle by way of the vicinity of the musculus gastrocnemius and/or the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over the musculus gastrocnemius and/or the musculus soleus so as to support the musculus gastrocnemius and the musculus soleus; the leg protection garment capable of supporting the musculus quadriceps femoris, namely, the muscle of the anterior side of the femoral region in an area above the knee region, and supporting the musculus gastrocnemius and the musculus soleus in an area below the knee region in addition to the support by the portion having a strong straining force (A) and/or (B) can be provided. Therefore, by such a combination, the leg protection garment can support, in particular, the muscles of the anterior side and the posterior side of the femoral region with balancing. As a result, the mutual functions of the muscles of the anterior side and the posterior side of the femoral region can efficiently be exhibited, and the functions of the articulatio genus and an entire function of the articulatio genus can be supported.

(6) Moreover, in the leg protection garment the present invention, by such a preferred embodiment where the portion having a strong straining force (D') comprises a lateral portion that ranges from the outside 31 of the hip to the patella region 36 by way of the portion 32 over the musculus glutaeus maximus, the trochanter major 2 and the portion over the tractus iliotibialis and/or the musculus vastus lateralis, and further ranges from the patella region 35 to the vicinity 16 of an area above the ankle by way of the vicinity over the musculus gastrocnemius and/or the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and further ranges from the patella region 35 to the vicinity 43 of an area above the ankle by way of the vicinity over the musculus gastrocnemius and/or the musculus soleus so as to support the musculus gastrocnemius and the musculus soleus; the leg protection garment capable of supporting the musculus glutaeus maximums, in addition to the effect of the above mentioned leg protection garment (5), can be provided.

(7) Moreover, by such a preferred embodiment where the leg protection garment of the present invention has a portion having a strong straining force (E) which ranges from the upper region 51 of the lateral crus located slightly below the patella region to the vicinity 54 of an area above the ankle by way of the vicinity over the musculus gastrocnemius and/or the musculus soleus so as to support the musculus gastrocnemius and the musculus soleus, wherein the portion passes the vicinity of the tendon region located below the musculus gastrocnemius without crossing the muscle belly of the musculus gastrocnemius at a right angle with respect to the direction of the muscle fiber; the leg protection garment capable of supporting the musculus gastrocnemius and the musculus soleus can be provided.

(8) Moreover, in the leg protection garment of the present invention, by such a preferred embodiment where the portion having a strong straining force is formed in a way in which a predetermined shaped stretchable fabric is overlapped with the garment's main part by stitching or adhering, a garment having durability can be easily manufactured.

(9) Moreover, in the leg protection garment of the present invention, by such a preferred embodiment where the portion having a strong straining force is formed in a way in which a predetermined shaped stretchable fabric is stretched and overlapped with the garment's main part by stitching or adhering, a stronger straining force can be provided to the portion having a strong straining force.

(10) Moreover, in the leg protection garment of the present invention, by such a preferred embodiment where the portion having a strong straining force is formed in a way in which elastic resin is impregnated or elastic resin film is adhered to the predetermined portion of the garment's main part, the portion having a strong straining force of a relatively thin thickness can be obtained.

(11) Moreover, in the leg protection garment of the present invention, by such a preferred embodiment where the portion having a strong straining force is a portion using an elastic fiber having a thicker thickness than that of any other location in the fiber material constituting the garment's main part since overlapping is not required, the portion having a strong straining force of a relatively thin thickness can be obtained.

(12) Moreover, in the leg protection garment of the present invention, by such a preferred embodiment where the portion having a strong straining force is a portion which comprises a texture of knitted fabric having a stronger straining force than texture of knitted fabric of stretchable fabric constituting the garment's main part, since overlapping is not required, the portion having a straining force of a relatively thin thickness can be obtained.

(13) Moreover, in the leg protection garment of the present invention, by such a preferred embodiment where the portion having a strong straining force has 30 to 400 gf of straining force, the effect of the present invention can efficiently be exhibited and an excellent fit can also be obtained without making a user feel too much compression.

(14) Moreover, in the leg protection garment of the present invention, by such a preferred embodiment where the stretchable fabric is a knitted fabric selected from the group consisting of a two directions stretchable tricot knitted fabric and stretchable rochelle knitted fabric, as compared with the conventional supporters etc. using the relatively thick pile fabric or neoprene sheet etc., the fabric having such a thickness as used for manufacturing the general garments can be used. Therefore, the leg protection garment having little deterioration of appearance, for example, a proportion in use; being well fitted to the body; and having excellent ventilation, can be provided.

Finally, it is understood that the invention may be embodied in other specific forms without departing from the spirit or essential characteristics thereof. The embodiments disclosed in this application are to be considered in all respects as illustrative and not restrictive, so that the scope of the invention being indicated by the appended claims rather than by the foregoing description, and all changes which come within the meaning and range of equivalency of the claims are intended to be embraced therein.

What is claimed is:

1. A leg protection garment having a lower half of the body part which has a leg portion of length capable of covering at least the patella region and formed of stretchable fabric, wherein said garment has a portion having a partially strong straining force and comprises the portion expressed by at least one selected from the group consisting of the following (A) and (B) as the portion having a strong straining force:

(A) a portion having a strong straining force which ranges from an area above the trochanter major 1 to the vicinity 5 of the upper end of the tibia by way of the trochanter major 2 and further the vicinity over the musculus biceps femoris so as to support the musculus biceps femoris, wherein said portion passes the vicinity 4 of the region located below the muscle belly of the musculus biceps femoris without crossing the muscle belly of the musculus biceps femoris at a right angle with respect to the direction of the muscle fiber;

(B) a portion having a strong straining force which ranges from an area 11 above the musculus semimembranous to the vicinity 14 of the upper end of the fibula by way of the vicinity over the musculus semimembranosus so as to support the musculus semitendinosus and the musculus semimembranosus, wherein said portion passes the vicinity 13 of the region located below the muscle belly of both the musculus semitendinosus and the musculus semimembranosus without crossing the muscle belly of the semitendinosus and the musculus semimembranosus at a right angle with respect to the direction of the muscle fiber.

2. The leg protection garment according to claim 1, wherein the portion (A) is a portion having a strong straining force which ranges from an area above the trochanter major 1 to the vicinity 5 of the upper end of the tibia by way of the trochanter major 2 and further the vicinity 3 of the boundary between the musculus biceps femoris and the tractus iliotibialis so as to support the musculus biceps femoris, wherein said portion obliquely crosses the vicinity 4 of the region located below the muscle belly of the musculus biceps femoris without crossing the muscle belly of the musculus biceps femoris.

3. The leg protection garment according to claim 1, wherein the portion (A) further has a portion having a strong straining force which, in an area above the trochanter majors, passes over at least one muscle selected from the group consisting of the musculus tensor fasciae latae, the tractus iliotibialis, and the musculus glutaeus medius.

4. The leg protection garment according to claim 3, wherein the portion (A) further has a portion having a strong straining force which ranges from the vicinity 5 of the upper end of the tibia to the vicinity 7 of the attaching region of the musculus semitendinosus and the musculus semimembranosus.

5. The leg protection garment according to claim 4, wherein the portion (B) is a portion having a strong straining force which ranges from an area 11 above the musculus semimembranosus to the vicinity 14 of the upper end of the fibula by way of the vicinity 12 of the boundary between the musculus semimembranosus and the musculus adductor magnus so as to support the musculus semitendinosus and the musculus semimembranosus, wherein said portion obliquely crosses over the vicinity 13 of the tendon region located below the muscle belly of both the musculus semitendinosus and the musculus semimembranosus without crossing the mauscle belly of the musculus semitendinosus and the musculus semimembranosus.

6. The leg protection garment according to claim 4 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over at least one selected from the group consisting of the musculus gastrocnemius and the musculus soleus so as to support the musculus gastrocnemius and the musculus soleus.

7. The leg protection garment according to claim 4 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus, so as to support the musculus gastrocnemius and the musculus soleus.

8. The leg protection garment according to claim 4 further having a portion having a strong straining force (D') comprising a lateral portion which ranges from the outside 31 of the hip to the patella region 35 by way of the portion 32 over the musculus glutaeus maximus, the trochanter major 2 and the vicinity over at least one selected from the group consisting of the tractus iliotibialis and the musculus vastus lateralis, and which further ranges from the patella region 35 to the vicinity 16 of an area above the ankle by way of at least one selected from the group consisting of the musculus gastrocnemius and the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and which further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

9. The leg protection garment according to claim 3, wherein the portion (B) is a portion having a strong straining force which ranges from an area 11 above the musculus semimembranosus to the vicinity 14 of the upper end of the fibula by way of the vicinity 12 of the boundary between the musculus semimembranosus and the musculus adductor magnus so as to support the musculus semitendinosus and the musculus semimembranosus, wherein said portion obliquely crosses over the vicinity 13 of the tendon region located below the muscle belly of both the musculus semitendinosus and the musculus semimembranosus without crossing the muscle belly of the musculus semitendinosus and the musculus semimembranosus.

10. The leg protection garment according to claim 9 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

11. The leg protection garment according to claim 3 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over at least one selected from the group consisting of the musculus gastrocnemius and the musculus soleus so as to support the musculus gastrocnemius and the musculus soleus.

12. The leg protection garment according to claim 3 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

13. The leg protection garment according to claim 3 further having a portion having a strong straining force (D') comprising a laterla portion which ranges from the outside 31 of the hip to the patella region 35 by way of the portion 32 over the musculus glutaeus maximus, the trochanter major 2 and the vicinity over at least the selected from the group consisting of the tractus iliotibialis and the musculus vastus lateralis, and which farther ranges from the patella region 35 to the vincity 16 of an area above the ankle by way of at least one selected from the group consisting of the musculus gastrocnemius and the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and which furthe ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

14. The leg protection garment according to claim 1, wherein the portion (A) further has a portion having a strong straining force which ranges from the vicinity 5 of the upper end of the tibia to the vicinity 7 of the attaching region of the musculus semitendinosus and the musculus semimembranosus.

15. The leg protection garment according to claim 14, wherein the portion (B) is a portion having a strong straining force which ranges from an area 11 above the musculus semimenibranosus to the vicinity 14 of the upper end of the fibula by way of the vicinity 12 of the boundary between the musculus semimembranosus and the musculus adductor magnus so as to support the musculus semitendinosus and the musculus semimembranosus, wherein said portion obliquely crosses over the vicinity 13 of the tendon region located below the muscle belly of both the musculus semitendinosus and the musculus semimembranosus without crossing the muscle belly of the musculus semitendinosus and the musculus semimembranosus.

16. The leg protection garment according to claim 15 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity of at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

17. The leg protection garment according to claim 14 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over at least one consisting of the musculus gastrocnemius and the musculus soleus so as to support the musculus gastrocnemius and the musculus soleus.

18. The leg protection garment according to claim 14 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

19. The leg protection garment according to claim 14 further having a portion having a strong straining force (D') comprising a lateral portion which ranges from the outside 31 of the hip to the patella region 35 by way of the portion 32 over the musculus glutaeus maximus, the trochanter major 2 and the vicinity over at least one selected from the group consisting of the tractus iliotibialis and the musculus vastus lateralis, and which further ranges from the patella region 35 to the vicinity 16 of an area above the ankle by way of at least one selected from the group consisting of the musculus gastrocnemius and the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and which further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

20. The leg protection garment according to claim 1, wherein the portion (B) is a portion having a strong straining force which ranges from an area 11 above the musculus semimembranosus to the vicinity 14 of the upper end of the fibula by way of the vicinity 12 of the boundary between the musculus semimembranosus and the musculus adductor magnus so as to support the musculus semitendinosus and the musculus semimembranosus, wherein said portion obliquely crosses over the vicinity 13 of the region located below the muscle belly of both the musculus semitendinosus and the musculus semimembranosus without crossing the muscle belly of the musculus semitendinosus and the musculus semimembranosus.

21. The leg protection garment according to claim 20 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over at least one selected from the group consisting of the musculus gastrocnemius and the musculus soleus so as to support the musculus gastrocnemius and the musculus soleus.

22. The leg protection garment according to claim 20 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus, and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

23. The leg protection garment according to claim 20 further having a portion having a strong straining force (D') comprising a lateral portion which ranges from the outside 31 of the hip to the patella region 35 by way of the portion 32 over the musculus glutaeus maximus, the trochanter major 2 and the vicinity over at least one selected from the group consisting of the tractus iliotibialis and the musculus vastus lateralis, and which further ranges from the patella region 35 to the vicinity 16 of an area above the ankle by way of at least one selected from the group consisting of the musculus gastrocnemius and the musculus soleus; and a medial portion which ranges from the medial side 38 of the femur to the patella region 35 by way of the portion 39 over the musculus vastus medialis so as to support the musculus vastus medialis, and which further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

24. The leg protection garment according to claim 1, wherein the portion (B) further has a portion having a strong straining force which ranges from the vicinity 14 of the upper end of the fibula to the vicinity 16 of an area above the ankle by way over the vicinity of at least one selected from the group consisting of the musculus gastrocnemius and the musculus soleus so as to support the musculus gastrocnemius and the musculus soleus.

25. The leg protection garment according to claim 1, wherein the portion (A) further has a portion having a strong straining force that ranges from the vicinity 5 of the upper end of the tibia to the vicinity 7 of the attaching region of the musculus semitendinosus and the musculus semimembranosus.

26. The leg protection garment according to claim 25 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over at least one selected from the group consisting of the musculus gastrocnemius and the musculus soleus so as to support the musculus gastrocnemius and the musculus soleus.

27. The leg protection garment according to claim 25 further having a portion having a strong straining force (D) comprising a lateral portion which ranges from the vicinity of the trochanter major to the patella region 35 by way of the vicinity over at least one selected from the group consisting of the tractus iliotibialis and musculus vastus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

28. The leg protection garment according to claim 25 further having a portion having a strong straining force (D') comprising a lateral portion which ranges from the outside 31 of the hip to the patella region 35 by way of the portion 32 over the musculus glutaeus maximus, the trochanter major 2 and the vicinity over at least one selected from the group consisting of the tractus iliotibialis and the musculus vastus lateralis, and which further ranges from the patella region 35 to the vicinity 16 of an area above the ankle by way of at least one selected from the group consisting of the musculus gastrocnemius and the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and which further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

29. The leg protection garment according to claim 13, wherein the portion (B') further has a portion having a strong straining force which ranges from the vicinity 14 of the upper end of the fibula to the vicinity 16 of an area above the ankle by way of the vicinity over at least one selected from the group consisting of the musculus gastrocnemius and the musculus soleus so as to support the musculus gastrocnemius and the musculus soleus.

30. The leg protection garment according to claim 1 further having a portion having a strong straining force (C) comprising a portion having a strong straining force which ranges from the upper region of the lateral crus 21 located proximally below the patella region to the vicinity 16 of an area above the ankle by way of the vicinity of at least one selected from the group consisting of the musculus gastrocnemius and the musculus soleus so as to support the musculus gastrocnemius and the musculus soleus; and a portion having a strong straining force which ranges from the upper region of the medial crus 22 located proximally below the patella region to the vicinity 24 of an area above the ankle by way of the vicinity over of at least one selected from the group consisting of the musculus gastrocnemius and the musculus soleus so as to support the musculus gastrocnemius and the musculus soleus.

31. The leg protection garment according to claim 1 further having a portion having a strong straining force (D) comprising a lateral portion which ranges from the vicinity of the trochanter major to the patella region 35 by way of the vicinity over at least one selected from the group consisting of the tractus iliotibialis and musculus lateralis, and further ranges from the patella region 35 to the vicinity 16 of an area above the ankle by way of the vicinity over at least one selected from the group consisting of the musculus gastrocnemius and the musculus soleus so as to support the musculus gastrocnemius and the musculus soleus; and a medial portion which ranges from the medial region of the femur 38 to the patella region 35 by way of the musculus vastus medialis 39 so as to support the musculus vastus medialis, and further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

32. The leg protection garment according to claim 1 further having a portion having a strong staining force (D') comprising a lateral portion which ranges from the outside 31 of the hip to the patella region 35 by way of the portion 32 over the musculus glutaeus maximus, the trochanter major 2 and the vicinity over at least one selected from the group consisting of the tractus iliotibialis and the musculus vastus lateralis, and which further ranges from the patella region 35 to the vicinity 16 of an area above the ankle by way of at least one selected from the group consisting of the musculus gastrocnemius and the musculus soleus so as to support the musculus gastrocnemius and the musculus soleus; and a medial portion which ranges from the medial side 38 of the femur to the patella region 35 by way of the portion 39 over the musculus vastus medialis so as to support the musculus vastus medialis, and which further ranges from the patella region 35 to the vicinity 43 of an area above the ankle by way of the vicinity over at least one selected from the group consisting of the musculus gastrocnemius and the musculus soleus so as to support the musculus gastrocnemius and the musculus soleus.

33. The leg protection garment according to claim 1 further having a portion having a strong straining force (E) which ranges from the upper region 51 of the lateral crus located proximally below the patella region to the vicinity 54 of an area above the ankle by way of the vicinity over at least one selected from the group consisting of the musculus gastrocnemius and the musculus soleus so as to support the musculus gastrocnemius and the musculus soleus, wherein the portion passes the vicinity of the region located below the musculus gastrocnemius without crossing the muscle belly of the musculus gastrocnemius at a right angle with respect to the direction of the muscle fiber.

34. The leg protection garment according to claim 1, wherein the portion having a strong straining force is formed in a way in which a predetermined shaped stretchable fabric is overlapped with the garment's main part by stitching or adhering.

35. The leg protection garment according to claim 1, wherein the portion having a strong straining force is formed in a way in which a predetermined shaped stretchable fabric is stretched and overlapped with the garment's main part by stitching or adhering.

36. The leg protection garment according to claim 1, wherein the portion having a strong straining force is formed in a way in which elastic resin is impregnated or elastic resin film is adhered to the predetermined portion of the garment's main part.

37. The leg protection garment according to claim 1, wherein the portion having a strong straining force is a portion using an elastic fiber having a thicker thickness than that of any other location in fiber material constituting the garment's main part.

38. The leg protection garment according to claim 1, wherein the portion having a strong straining force is a portion which comprises texture of a knitted fabric having a stronger straining force than texture of a knitted fabric of stretchable fabric constituting the garment's main part.

39. The leg protection garment according to claim 1, wherein the portion having a strong straining force has a straining force of 30 to 400 gf.

40. The leg protection garment according to claim 1, wherein the stretchable fabric is a knitted fabric selected from the group consisting of a two directions stretchable tricot knitted fabric and a stretchable rochelle knitted fabric.

41. A leg protection garment having a lower half of the body part which has a leg portion of length capable of covering at least the patella region and formed of stretchable fabric, wherein said garment has a portion having a partially strong straining force and comprises the portion expressed by at least the following (A) and (B') as the portion having a strong straining force:

(A) a portion having a strong straining force which ranges from an area above the trochanter major 1 to the vicinity 5 of the upper end of the tibia by way of the trochanter major 2 and further the vicinity over the musculus biceps femoris so as to support the musculus biceps femoris from the side, wherein said portion passes the vicinity 4 of the region located below the muscle belly of the musculus biceps femoris without crossing the muscle belly of the musculus biceps femoris at a right angle with respect to the direction of the muscle fiber;

(B') a portion having a strong straining force which ranges from the vicinity 13 of the region located below the muscle belly of both the musculus semitendinosus and musculus semimembranosus to the vicinity 14 of the upper end of the fibula.

42. The leg protection garment according to claim 41, wherein the portion (A) further has a portion having a strong straining force, in an area above the trochanter major, which passes over at least one muscle selected from the group consisting of the musculus tensor fasciae latae, the tractus iliotibialis, and the musculus glutaeus medius.

43. A leg protection garment having a lower half of the body part which has a leg portion capable of covering at least the patella region and formed of a stretchable fabric, wherein said garment has a portion having a partially strong straining force and comprises the portion expressed by at least the following (A') and (B) as the portion having a strong straining force:

(A') a portion having a strong straining force which ranges from the vicinity 4 of the region located below the muscle belly of the musculus biceps femoris to the vicinity 5 of the upper end of the tibia;

(B) a portion having a strong straining force which ranges from an area 11 above the musculus semimembranosus to the vicinity 14 of the upper end of the fibula by way of the vicinity over the musculus semimembranosus so as to support the musculus semitendinosus and the musculus semimembranosus, wherein said portion passes the vicinity 13 of the region located below the muscle belly of both the musculus semitendinosus and the musculus semimembranosus without crossing the muscle belly of the musculus semitendinosus and the musculus semimembranosus at a right angle with respect to the direction of the muscle fiber.

44. The leg protection garment according to claim 43, wherein the portion (A') further has a portion having a strong straining force which ranges from the vicinity 5 of the upper end of the tibia to the vicinity 7 over the attaching region of the musculus semitendinosus and the musculus semimembranosus.

45. The leg protection garment according to claim 43, wherein the portion (B) further has a portion straining force which ranges from the vicinity 14 of the upper end of the fibula to the vicinity 16 of an area above the ankle by way of the vicinity of at least one selected from the group consisting of the musculus gastrocnemius and the musculus soleus so as to support the musculus gastrocnemius and the musculus soleus.

* * * * *